US012594109B2

(12) United States Patent
Sweitzer et al.

(10) Patent No.: US 12,594,109 B2
(45) Date of Patent: Apr. 7, 2026

(54) SURGICAL EXTRACTOR WITH A RATCHETING HANDLE DEVICE

(71) Applicant: Shukla Medical, St. Petersburg, FL (US)

(72) Inventors: Zachary Robert Sweitzer, Keyport, NJ (US); Adam Gosik-Wolfe, Tampa, FL (US)

(73) Assignee: Shukla Medical, St. Petersburg, FL (US)

( * ) Notice: Subject to any disclaimer, the term of this patent is extended or adjusted under 35 U.S.C. 154(b) by 380 days.

(21) Appl. No.: 18/161,943

(22) Filed: Jan. 31, 2023

(65) Prior Publication Data

US 2024/0252221 A1     Aug. 1, 2024

(51) Int. Cl.
A61B 17/88 (2006.01)
A61B 17/00 (2006.01)

(52) U.S. Cl.
CPC ..................... A61B 17/8888 (2013.01); A61B 2017/00407 (2013.01)

(58) Field of Classification Search
CPC ............ A61B 17/8875; A61B 17/8888; A61B 17/8891; A61B 2017/00407
See application file for complete search history.

(56) References Cited

U.S. PATENT DOCUMENTS

| | | | |
|---|---|---|---|
| 2006/0069407 A1* | 3/2006 | Weber ................ | A61B 17/0483 606/205 |
| 2006/0243108 A1* | 11/2006 | Lechot ................ | B25B 23/0042 82/52 |
| 2012/0116466 A1 | 5/2012 | Dinville et al. | |
| 2013/0023911 A1 | 1/2013 | Esanu | |
| 2021/0290411 A1* | 9/2021 | Gosik-Wolfe ........ | A61F 2/4603 |

FOREIGN PATENT DOCUMENTS

WO      2000023012 A1    4/2000

OTHER PUBLICATIONS

European Patent Office, Office Action issued in counterpart EP Application No. 24151495, dated Apr. 16, 2025.
IP Australia, Examination Report issued in counterpart AU Application No. 2024200100, dated May 26, 2025.
European Patent Office, European Search Report in counterpart EP Application No. 24151495, dated Jun. 18, 2024.

* cited by examiner

*Primary Examiner* — Samuel S Hanna
(74) *Attorney, Agent, or Firm* — Kim IP Law Group LLC

(57)          ABSTRACT

A surgical extractor including an extractor device having a proximal end and a distal end, a first jaw and a second jaw configured to engage a fastener and carried at the distal end of the extractor device, and a ratchet handle device extending from the proximal end of the extractor device.

7 Claims, 30 Drawing Sheets

SURGICAL EXTRACTOR WITH A RATCHETING HANDLE DEVICE

BACKGROUND

In an operating room, it is difficult and time consuming to remove broken or stripped bone screws from a patient. Often, the bone needs to be cored down around the screw, and secondary tools are used to remove the bone screw. For example, pliers may be used to grip and twist the exposed screws out. In this case, however, slippage in gripping the screws often results, leading to added surgical time for screw removal. Also, the repetitive nature in gripping the screw, rotating the pliers to twist the screw with a user's wrist, releasing the screw, and regripping the screw for additional rotations results in user fatigue. All of these issues add to the overall time a patient spends in the operating room.

SUMMARY

According to an exemplary embodiment of the subject disclosure, there is provided a surgical extractor comprising an extractor device having a proximal end and a distal end, a first jaw and a second jaw configured to engage a fastener and carried at the distal end of the extractor device, and a ratchet handle device extending from the proximal end of the extractor device.

According to an aspect, the extractor device comprises a first arm, a second arm, and a link pivotably connected to the first and second arms. According to another aspect, the first arm has a proximal end and a distal end, a quick connect at the proximal end thereof for operatively engaging the ratchet handle device, the distal end of the first arm being configured for attachment to the first jaw. According to another aspect, the link has a distal end configured for attachment to the second jaw.

According to an aspect, the ratchet handle device comprises a ratchet assembly, a handle shaft including splines, wherein the handle shaft extends proximally from the ratchet assembly, and a quick connect coupling for engaging the quick connect of the first arm. According to another aspect, the handle shaft is operable to rotate relative to the ratchet assembly.

According to an aspect, the ratchet assembly comprises a housing, a first pawl within the housing configured to engage the handle shaft splines from a first direction and arrest rotation of the handle shaft in a first rotational direction, and a first biasing member within the housing biasing the first pawl into engagement with the handle shaft splines. According to another aspect, the ratchet assembly further comprises a second pawl within the housing configured to engage the handle shaft splines form a second direction opposite the first direction and arrest rotation of the handle shaft in a second rotational direction opposite the first rotational direction, and a second biasing member within the housing biasing the second pawl into engagement with the handle shaft splines. According to another aspect, the ratchet assembly further comprises an actuator for selectively disengaging the first pawl and the second pawl from the handle shaft splines to permit rotation of the handle shaft in either the first rotational direction or the second rotational direction.

According to an aspect, the housing comprises opposed flat surfaces and the quick connect of the first arm comprises oppositely directed flat surfaces configured to matingly engage with the opposed flat surfaces of the housing to prevent relative rotation between the housing and the extractor device.

According to an aspect, the handle shaft includes a grip at a proximal end thereof. According to another aspect, the grip extends substantially transverse to the handle shaft.

According to an aspect, each of the first and second jaws comprises a plurality of longitudinally extending ridges. According to another aspect, each of the first and second jaws further comprises a plurality ridges extending transversely to the plurality of longitudinally extending ridges.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the invention, there are shown in the drawings exemplary embodiments. It should be understood, however, that the exemplary embodiments are not limited to the precise arrangements and instrumentalities shown.

DETAILED DESCRIPTION OF THE INVENTION

Figure 1:
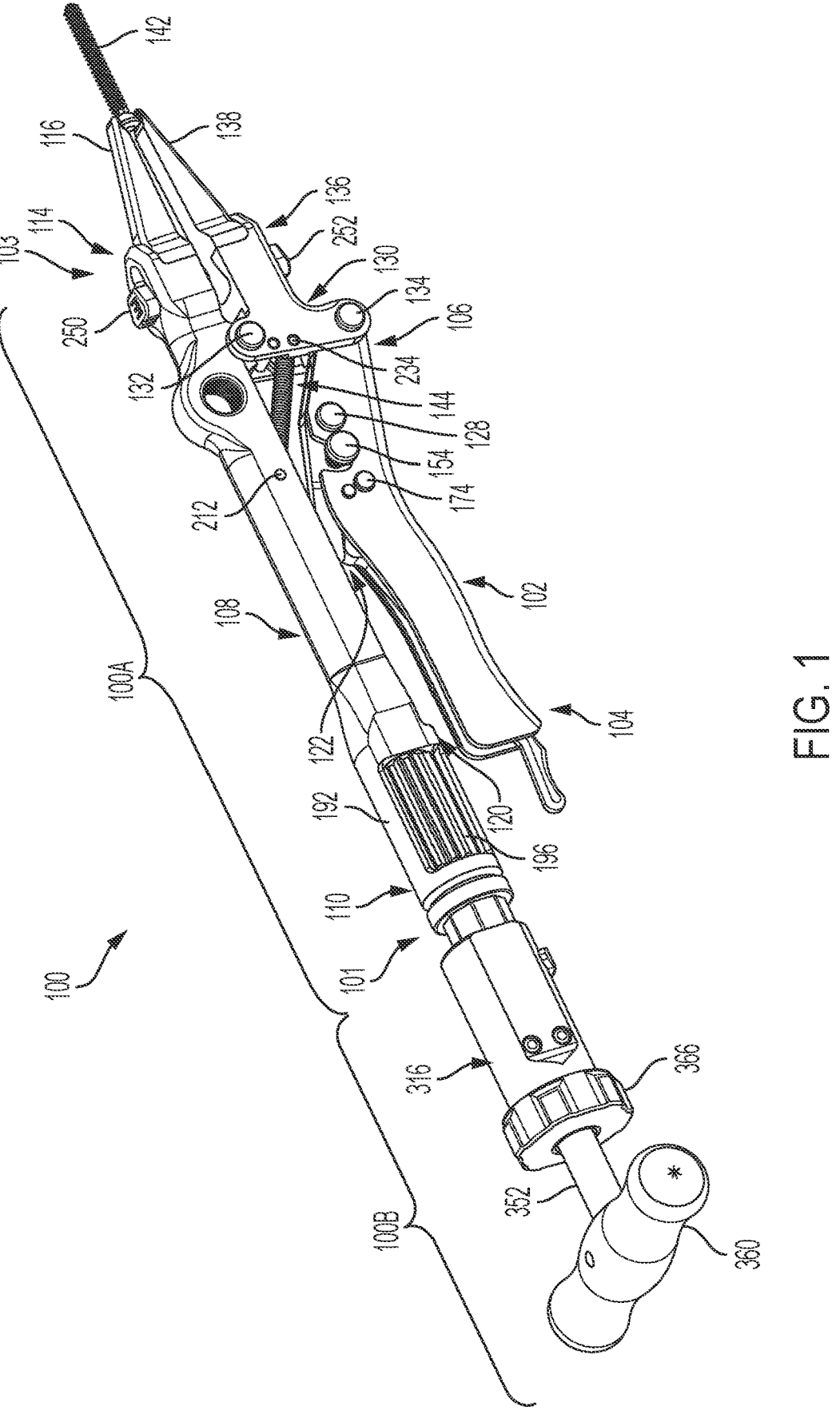
FIG. 1 is a perspective view of a surgical extractor in accordance with an exemplary embodiment of the subject disclosure shown gripping a surgical screw.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2:
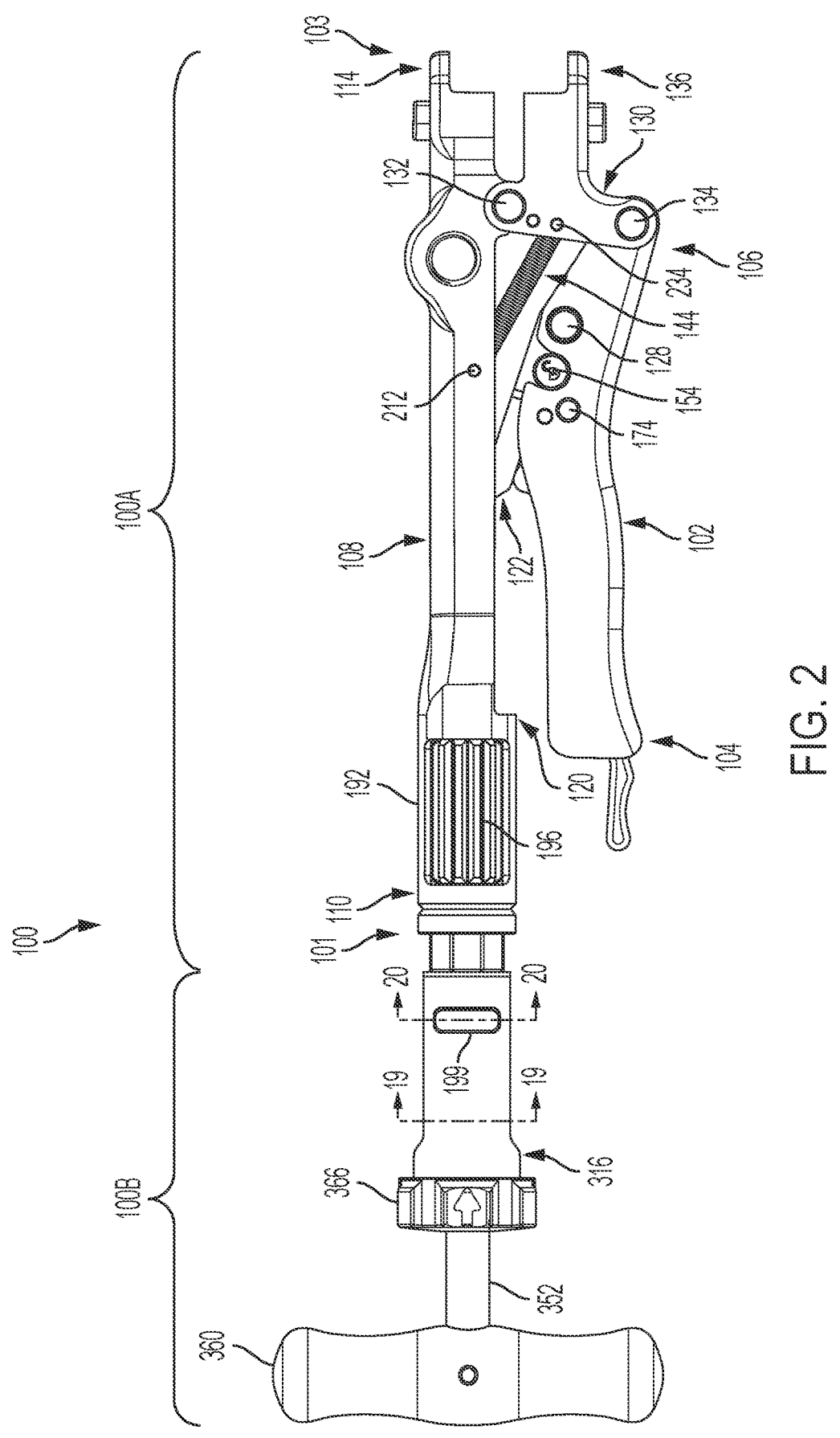
FIG. 2 is a side view of the surgical extractor of FIG. 1.
Figure 3:
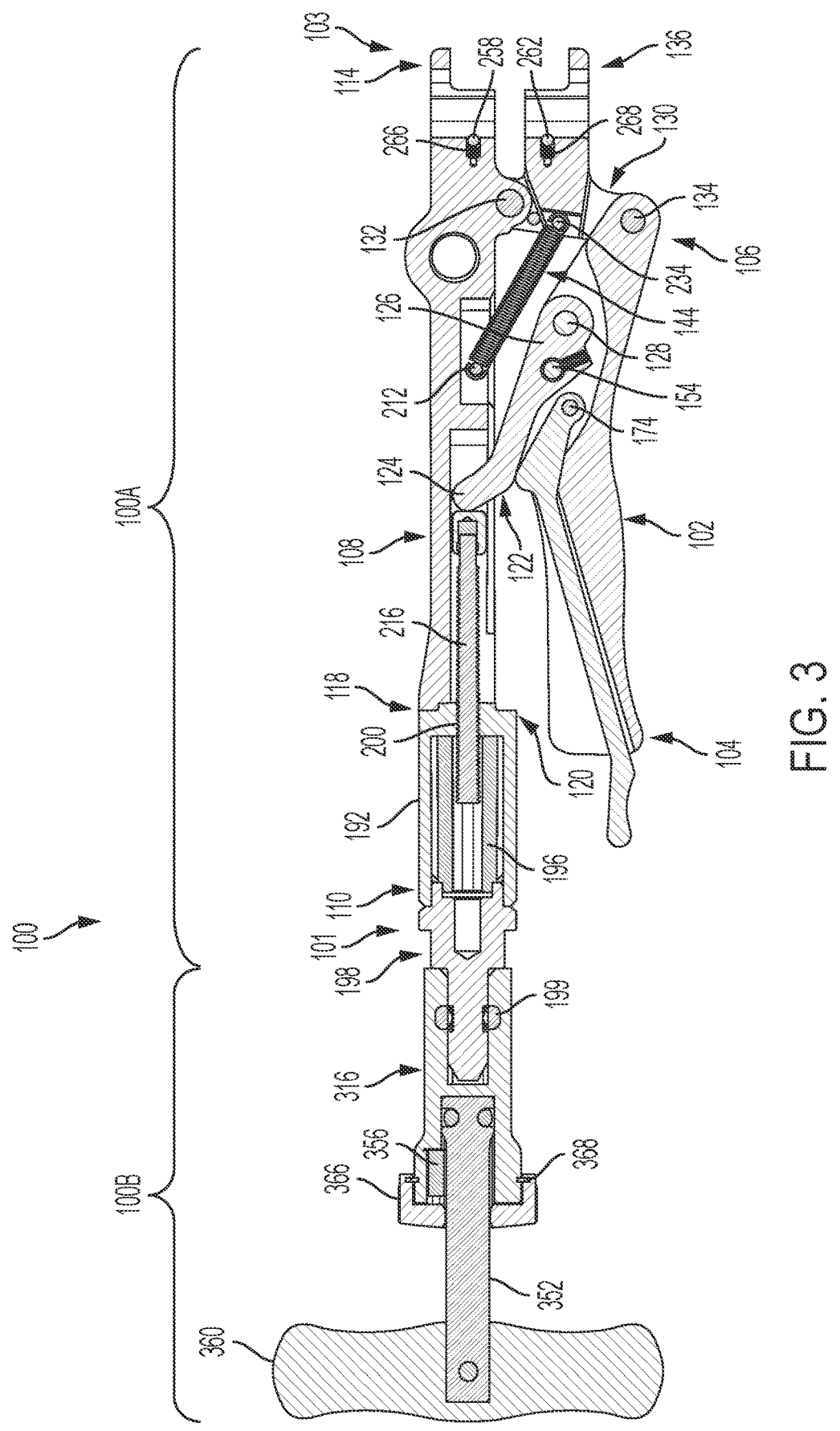
FIG. 3 is a longitudinal cross-sectional view of the extractor of FIG. 1.

Referring now to the drawings, FIGS. 1-3 illustrate a surgical extractor 100 in accordance with an exemplary embodiment of the subject disclosure. The surgical extractor includes an extractor device 100A having a proximal end 101 and a distal end 103, a pair of jaws 116, 138 configured to engage a fastener 142 and carried at the distal end of the extractor device, and a ratchet handle device 100B extending from the proximal end of the extractor device. The ratchet handle device can be fixed to the extractor device. However, as described below in connection with an exemplary embodiment of the subject disclosure, the ratchet handle device can be releasably attachable to the extractor device.

The extractor device 100A includes a second arm 102 having a proximal end 104 and a distal end 106, and a first arm 108 having a proximal end 110 for attachment to ratchet handle device 100B. In particular, the first arm 108 includes a quick connect 300 at the proximal end thereof for operatively engaging the ratchet handle device. The first arm additionally has a distal end 114 configured for attachment to a first jaw 116, and an adjustment mechanism 118 including an adjuster 120 and a lever 122. The lever has a proximal end 124 engaged with the adjuster and a distal end 126 pivotably connected to the second arm 102 via pivot pin 128. The extractor device 100A additionally comprises a link 130 pivotably connected to the first and second arms via pivot pins 132, 134, the link having a distal end 136 configured for attachment to a second jaw 138.

Figures 4A, 4B:
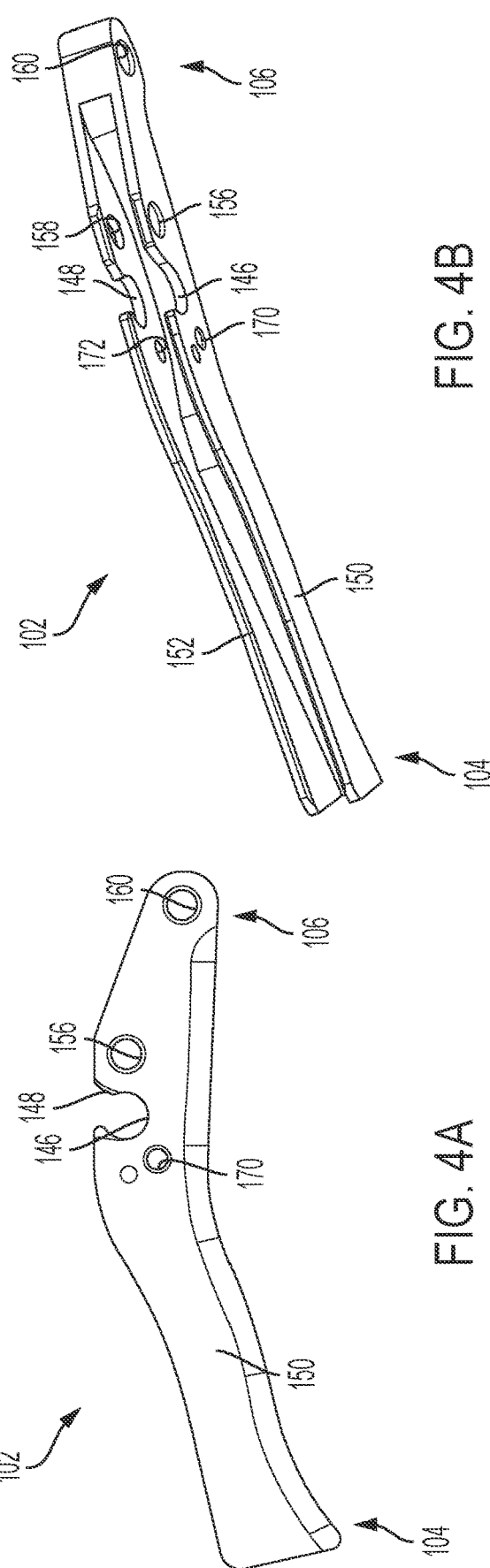
FIG. 4A is side view of a second arm of the surgical extractor of FIG. 1.
FIG. 4B is a perspective view of the second arm of FIG. 4A.

The second arm 102 is configured as best shown in FIGS. 4A and 4B, and is constructed as an elongated arm having a channel formed by upstanding sidewalls 150, 152. About its midportion the second arm is provided with a pair of notches 146, 148 in the upstanding side walls 150, 152 which are adapted to cooperate with a locking mechanism 154 (described below in connection with FIGS. 16 and 17) carried by the lever 122. The side walls 150, 152 further include a first pair of aligned openings 156, 158 that receive the pivot pin 128 for pivotably connecting the distal end 126 of the lever 122 to the second arm. About the distal end 106 of the second arm is a through bore 160 that aligns with aligned openings 162, 164 provided in the lower branches 166, 168 of the link 130 (FIGS. 9A-9C) to receive the pivot pin 134 to pivotably connect the distal end of the second arm 102 to the lower branches of the link. Additionally, the side walls 150, 152 include a second pair of aligned openings 170, 172 that receive a pivot pin 174 (FIGS. 1-3) that likewise passes through a through bore 176 provided at a distal end 178 of a release lever 180 (FIG. 16) for pivotably connecting the distal end of the release lever to the second arm. The function of the release lever 180 is described in greater detail in connection with FIG. 16.

Figure 5A:
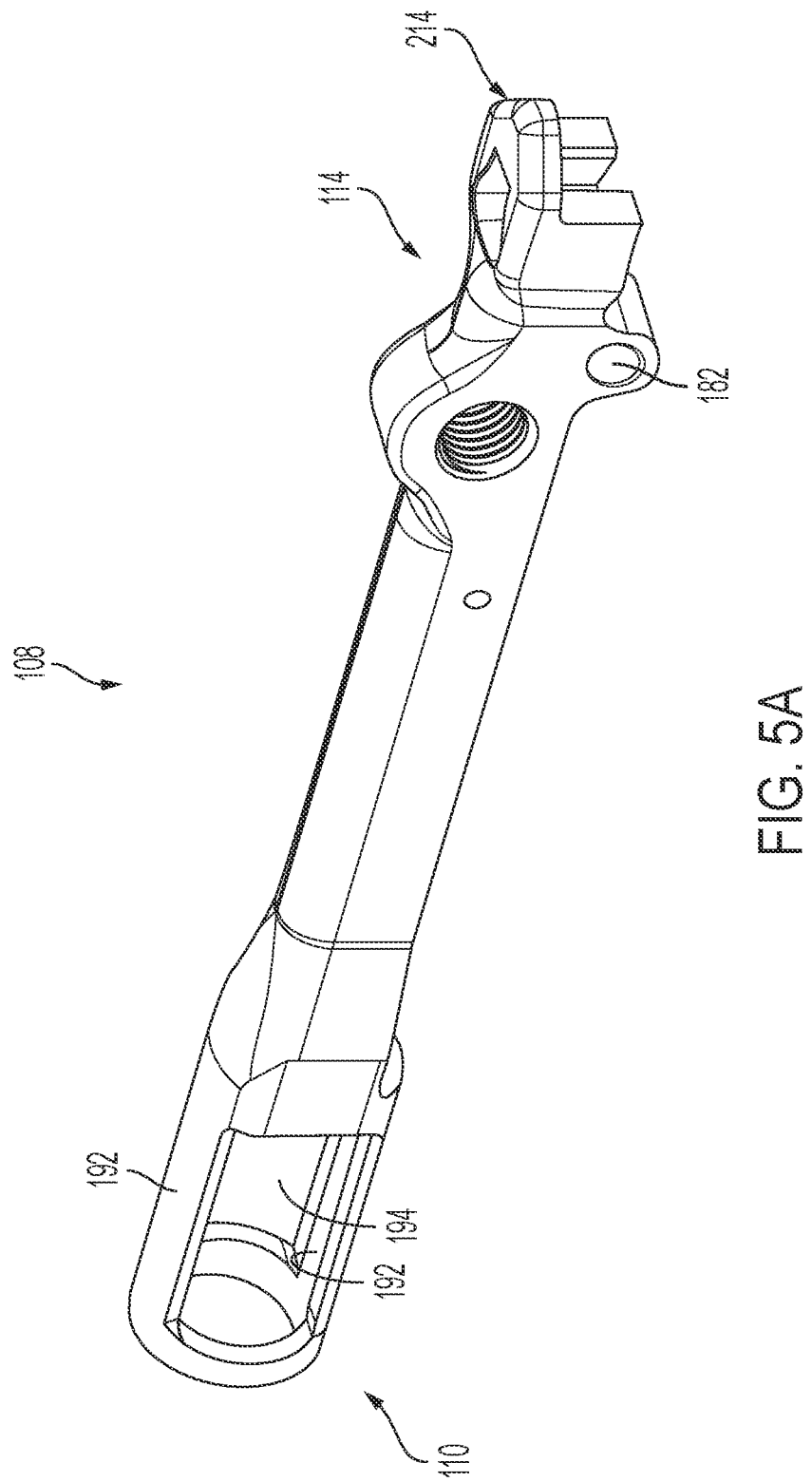
FIG. 5A is a front perspective view of a first arm of the surgical extractor of FIG. 1.
Figure 5B:
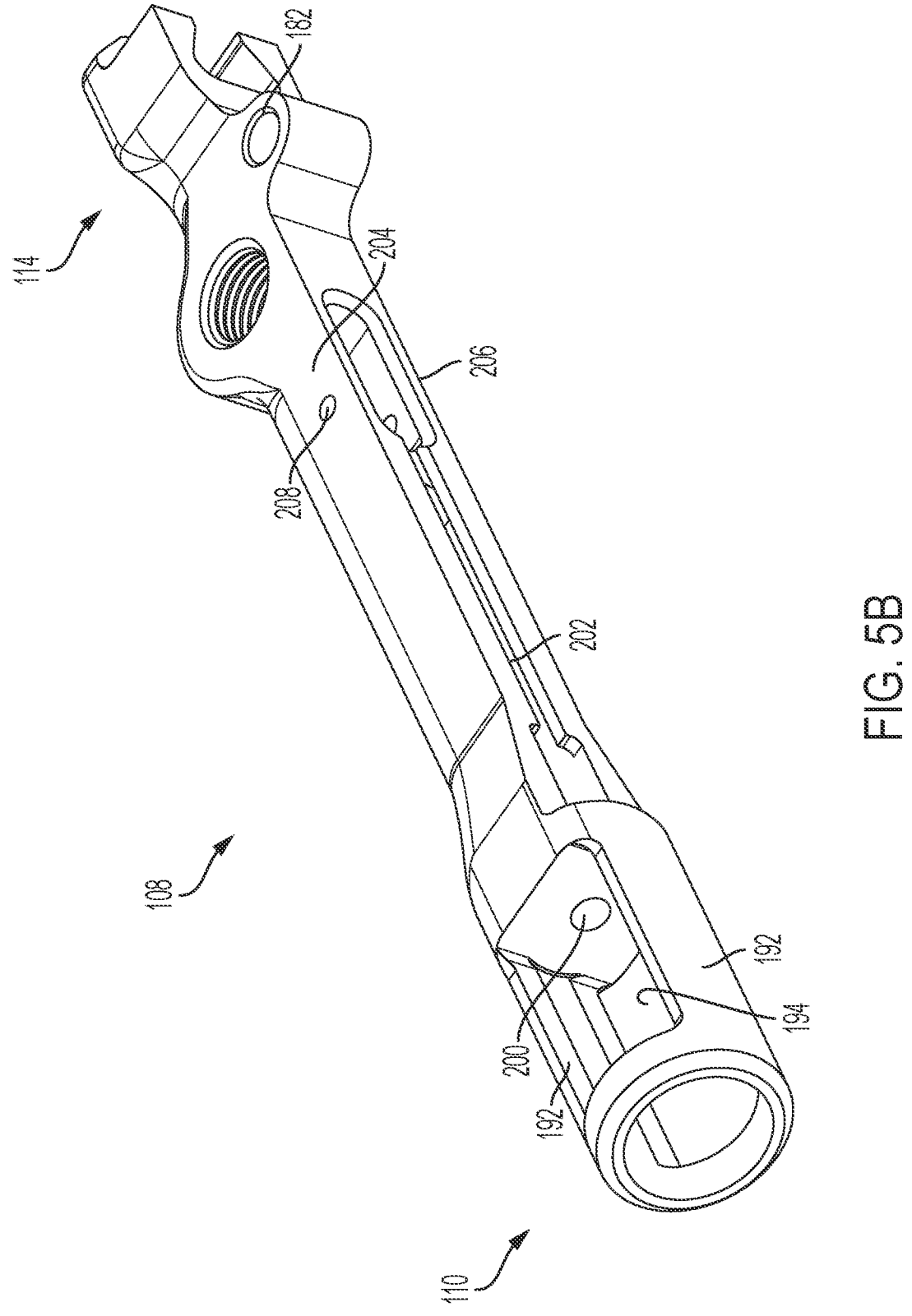
FIG. 5B is a front perspective view of the first arm of FIG. 5A.
Figure 5C:
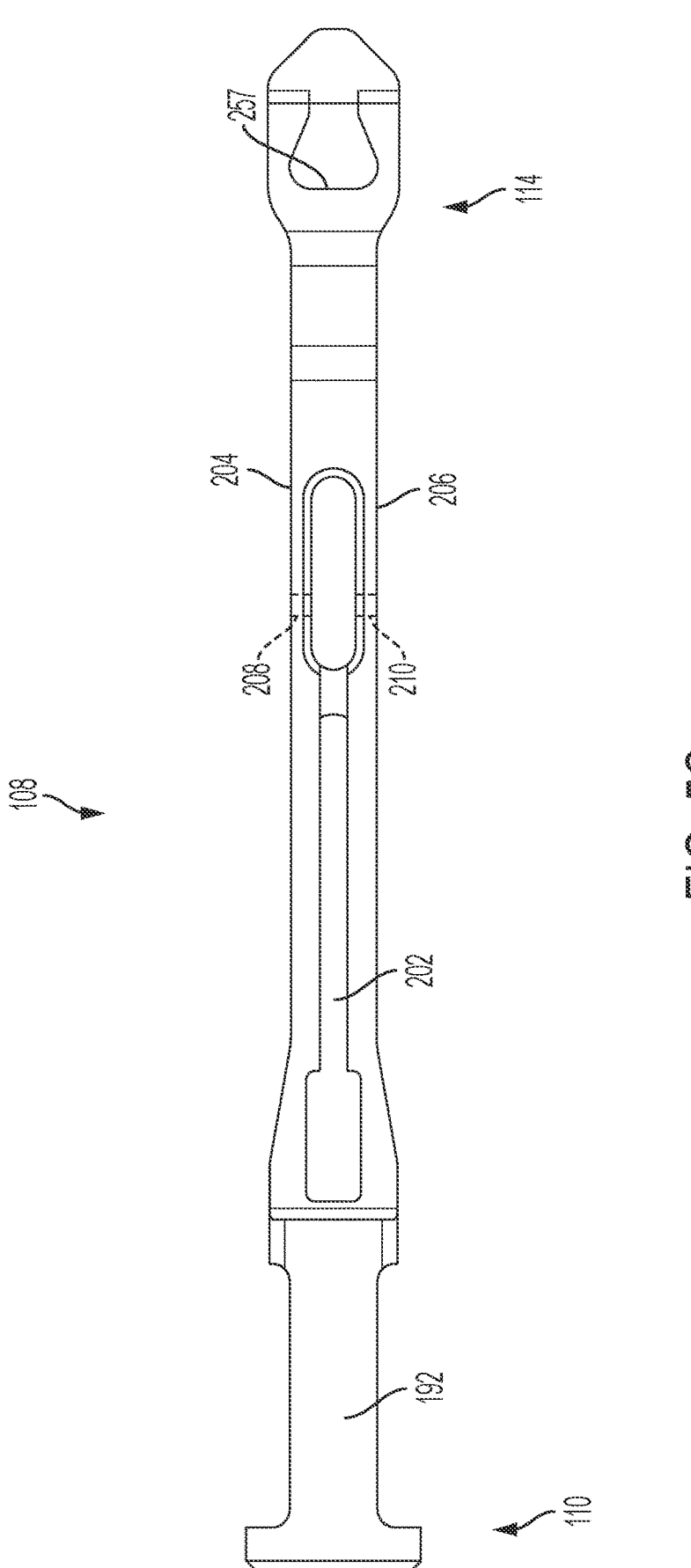
FIG. 5C is a bottom view of the first arm of FIG. 5A.

The construction of the first arm 108 is configured as best shown in FIGS. 5A-5E. Adjacent the distal end 114 of the first arm there is provided a through bore 182 that aligns with aligned openings 184, 186 provided in the upper branches 188, 190 of the link 130 (FIGS. 9A-9C) to receive the pivot pin 132 to pivotably connect the distal end of the first arm 108 to the upper branches of the link. Near the proximal end 110, the first arm body includes a cage 192 having an opening or hollow interior 194 for housing a rotatable knob 196 which forms part of the adjuster 120 of the adjustment mechanism 118 (see also FIGS. 1-3, 7A and 7B). Adjacent a distal end of the cage 192 is an internally threaded through bore 200 (FIGS. 3, 5B, 5D and 5E). The through bore 200 is in communication with the cage 192 and with a slot 202 (FIGS. 5C-5E) structured to house a rod 216, as further discussed below. Adjacent the slot 202 the first arm includes a pair of side walls 204, 206 that are provided with aligned openings 208, 210 (FIGS. 5B and 5C) to receive a pin 212 which holds a first end of a biasing member 144 (FIGS. 1-3). As shown in FIG. 5A, at the tip of the distal end 114, the first arm includes a slidable lock 214 for attachment to the first jaw 116, which is discussed in further detail below.

Figure 20:
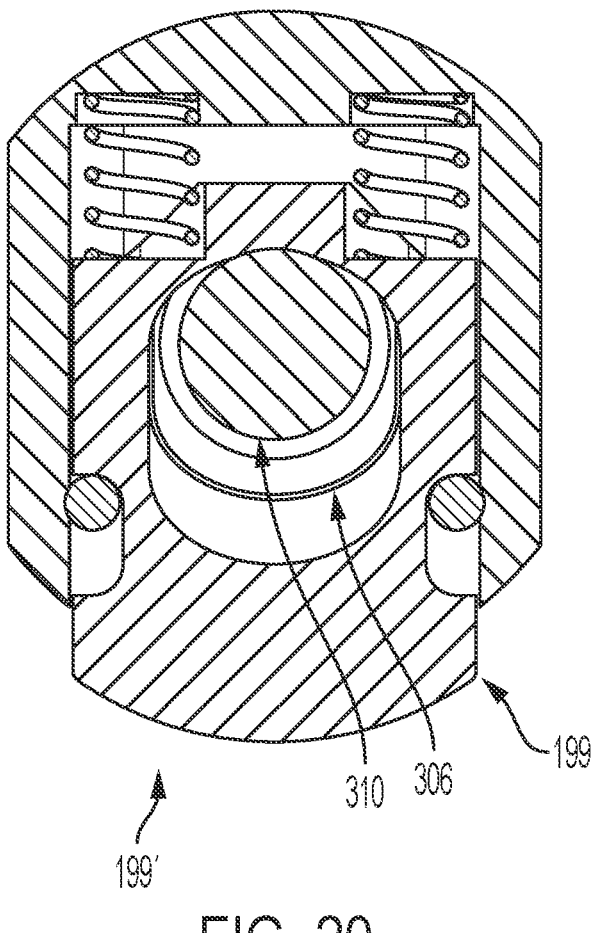
FIG. 20 is a cross-sectional view taken along line 20-20 of FIG. 2 showing a quick connect coupling of the ratchet housing of FIGS. 18A-18C engaging a reduced diameter portion of the quick connect of FIGS. 17A-17C.

The first arm also includes a quick connect 198 (FIGS. 3 and 17A-17C) about its proximal end structured to releasably engage with, e.g., a corresponding quick connect coupling carried by the ratchet handle device 100B. The corresponding quick connect coupling includes a biased locking member 199 (FIGS. 2, 3 and 20).

Figures 5D, 5E:
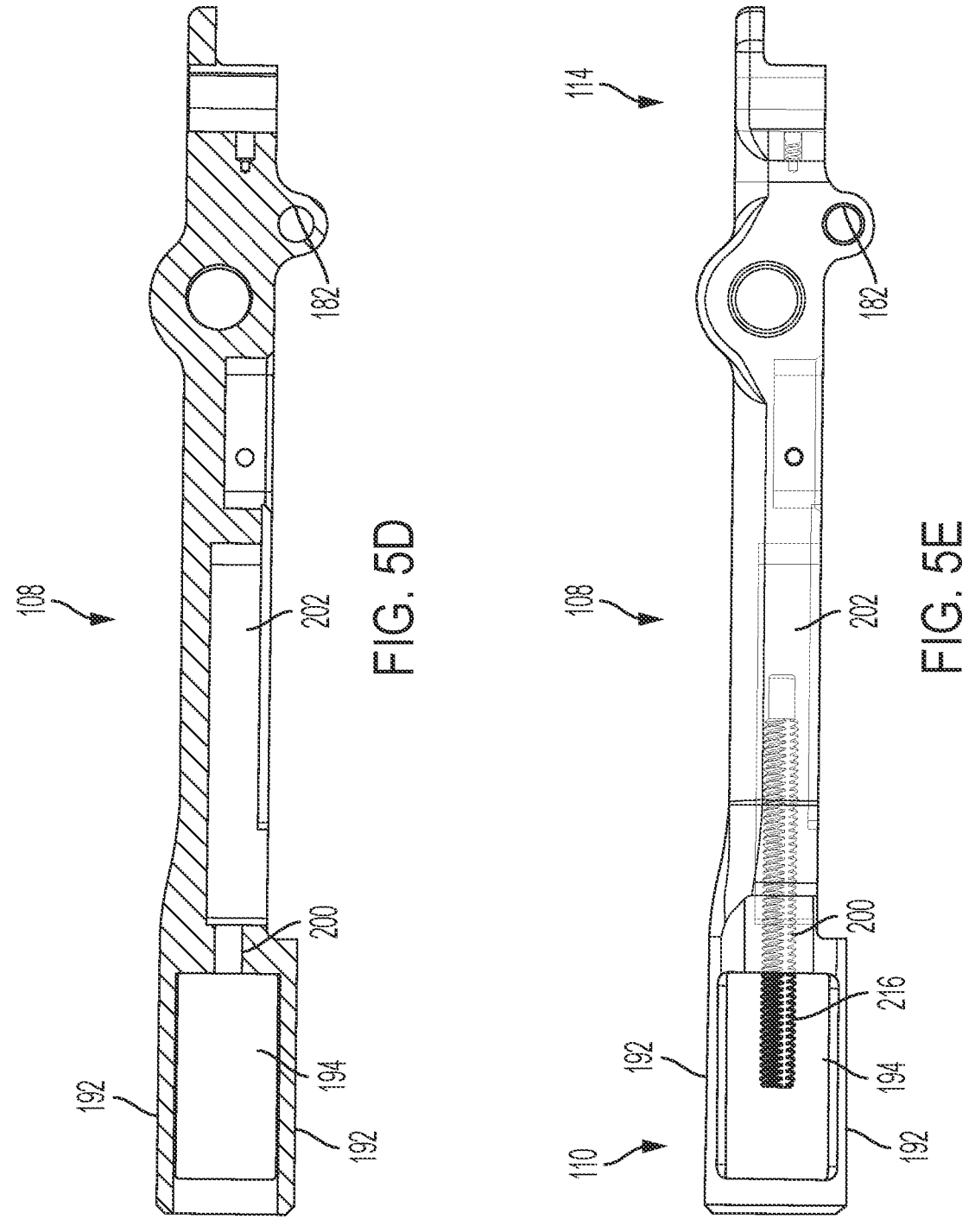
FIG. 5D is a cross-sectional side view of the first arm of FIG. 5A.
FIG. 5E is a side view of the first arm of FIG. 5A including a threaded rod threadedly engaging the first arm.
Figure 6B:
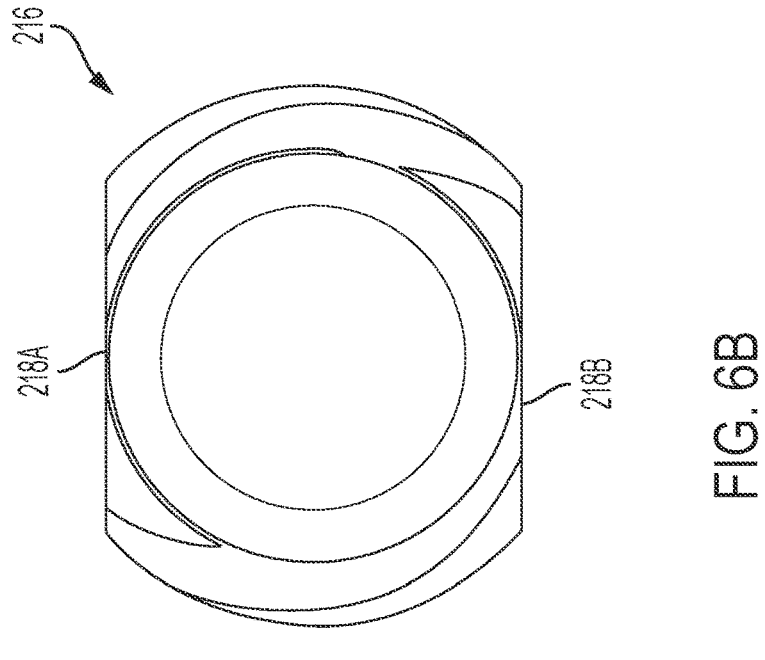
FIG. 6B is an end view of the threaded rod of FIG. 6A.
Figure 6A:
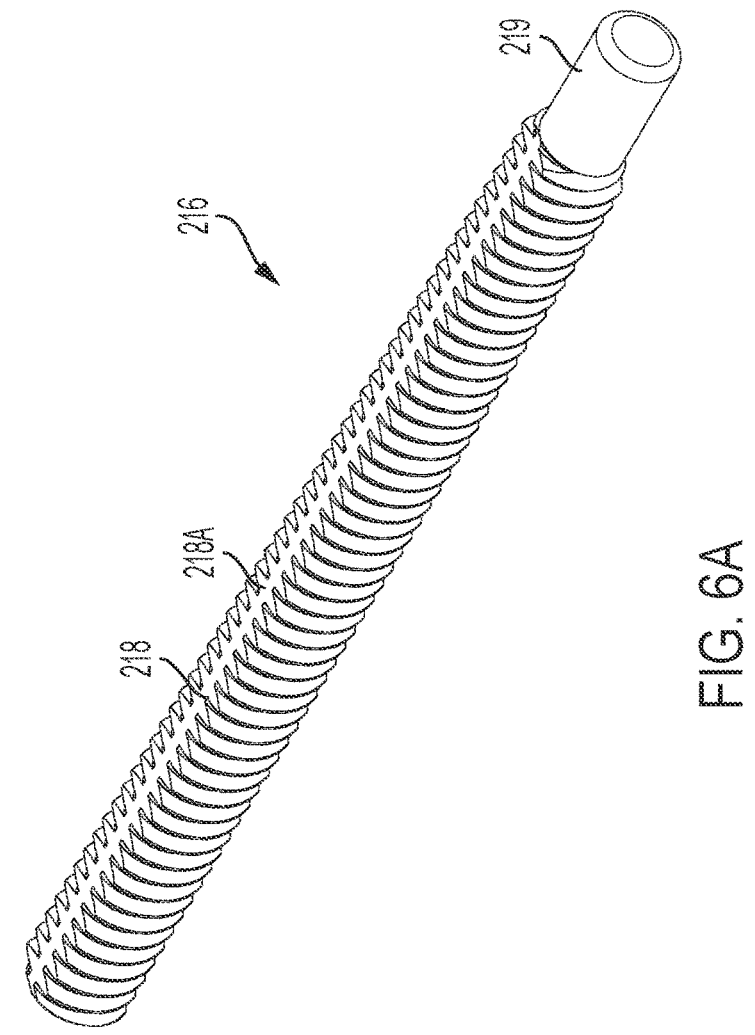
FIG. 6A is a perspective view of a threaded rod of an adjuster of the surgical extractor of FIG. 1.

FIG. 3 best illustrates the adjustment mechanism 118 of the first arm 108. The adjustment mechanism includes the adjuster 120 and the lever 122. The adjuster comprises the rotatable knob 196 and the rod 216. The rod 216 extends from the rotatable knob and is movable relative to the rotatable knob. The rod 216 is a threaded rod (FIGS. 5E, 6A and 6B) threadedly engaged with the first arm at the internally threaded through bore 200 as shown in FIG. 5E. The rod 216 includes at least one planar side 218, and preferably a pair of opposing planar sides 218A, 218B. The rod also includes a non-threaded distal nose 219. The rod is sized in length sufficiently such that the distal nose 219 of the rod 216 abuts the proximal end 124 of the lever 122.

Figure 7B:
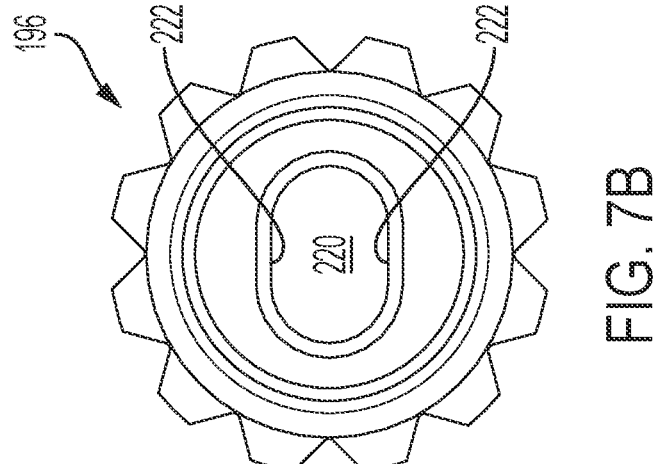
FIG. 7B is an end view of the rotatable knob of FIG. 7A.
Figure 7A:
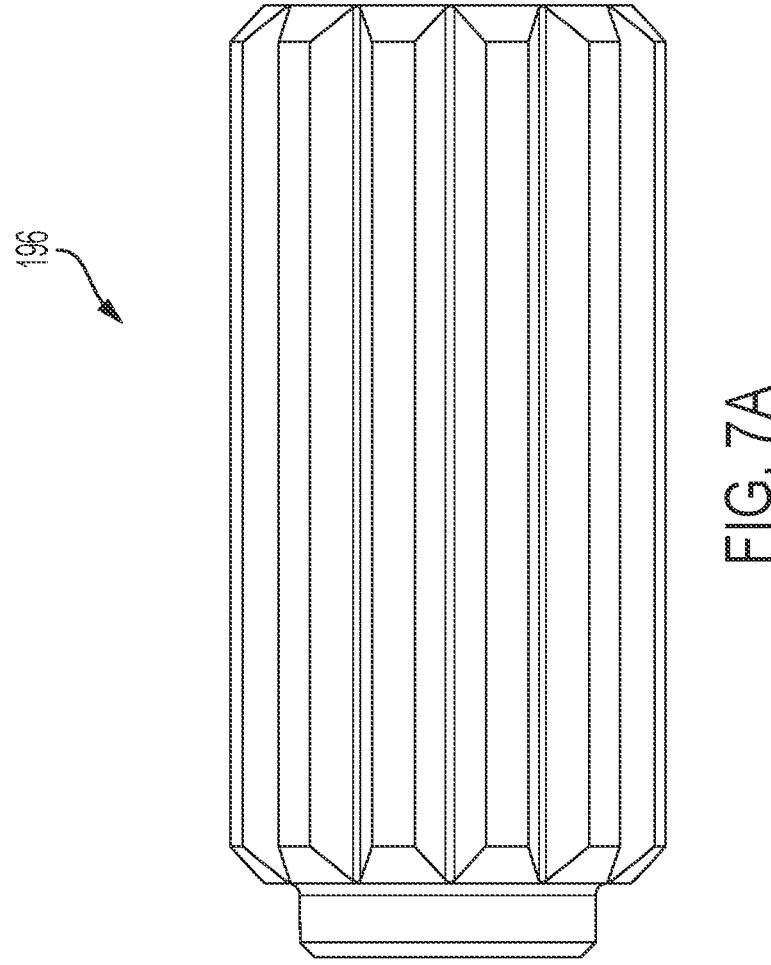
FIG. 7A is a side view of a rotatable knob of an adjuster of the surgical extractor of FIG. 1.

The rotatable knob 196 is configured as best shown in FIGS. 7A and 7B having a generally cylindrical configuration. The outer surface of the rotatable knob is preferably textured, e.g. with splines, knurling or the like, to enhance gripping of a user's fingers when rotating the rotatable knob. As shown in FIG. 7B, the rotatable knob 196 has an opening 220 about its end or proximally facing end, with a planar side 222 to cooperate with the planar side 218 of the rod 216. Rotation of the rotatable knob 196 causes rotation of the threaded rod 216 within the internally threaded through bore 200, thereby causing the rod 216 to extend from or retract into the rotatable knob depending on the direction of rotation of the rotatable knob, or in other words move along a direction of a longitudinal axis of the rod. More particularly, rotation of the rotatable knob 196 in a first direction causes the rod 216 to extend from the rotatable knob. In so doing, the distal nose 219 of the rod pushes further against the proximal end 124 of the lever 122. Conversely, rotation of the rotatable knob 196 in a second direction causes the rod 216 to retract into the rotatable knob. In so doing, the proximal end 124 of the lever 122 remains in contact with the distal nose 219 of the rod 216 since it is under the influence of the biasing member 144, discussed below.

Figure 8:
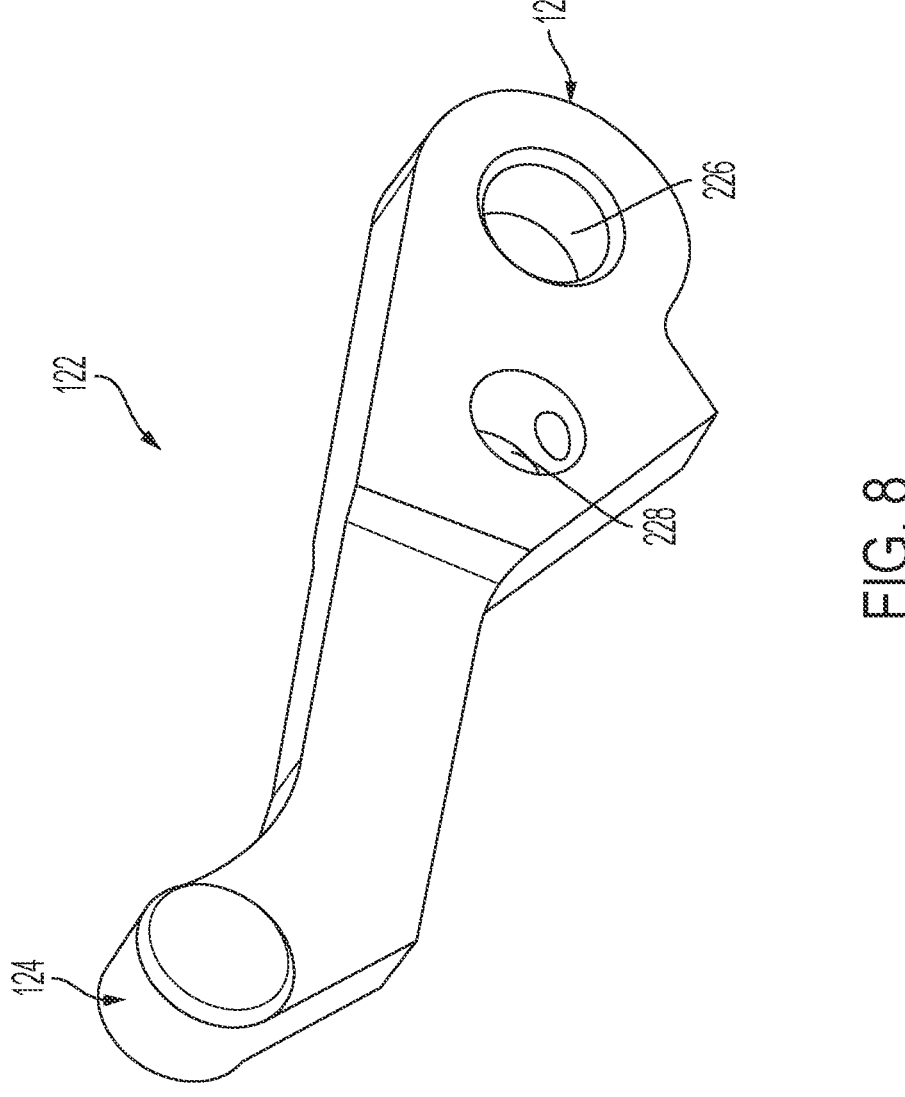
FIG. 8 is a left perspective view of a lever of the surgical extractor of FIG. 1.

The lever 122 is structured as best shown in FIGS. 3 and 8. Referring to FIG. 8, between its proximal and distal ends 124, 126, the lever 122 includes a first through bore 226 that receives the pivot pin 128 for pivotably connecting the distal end 126 of the lever 122 to the second arm (FIG. 3). The lever 122 further includes a second through bore 228 through which the locking mechanism 154 passes (see FIGS. 3 and 13).

Figures 9A, 9B, 9C:
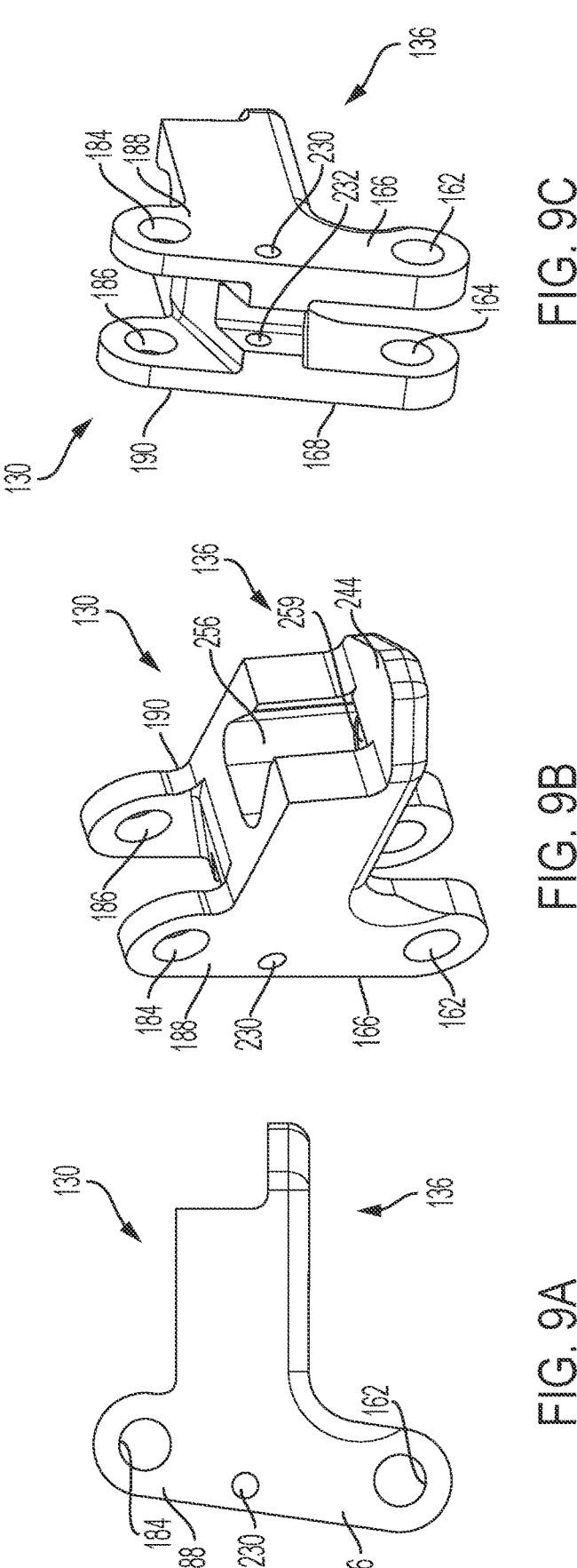
FIG. 9A is a side view of a link of the surgical extractor of FIG. 1.
FIG. 9B is a front perspective view of the link of FIG. 9A.
FIG. 9C is a rear perspective view of the link of FIG. 9A.

FIGS. 9A-9C best show the construction of the link 130. The link includes upper and lower branches. Between the upper branches 188, 190 and lower branches 166, 186, the link includes a pair of aligned through bores 230, 232. The through bores 230, 232 receive a pin 234 which holds a second end of the biasing member 144 (FIGS. 1-3). The distal end 136 of the link 130 is provided with a fastener 256 for attaching the second jaw 138 to the link. Likewise, the distal end 114 of the first arm 108 is provided with a fastener 254 for attaching the first jaw 116 to the first arm. As shown in FIG. 9B the link includes an aperture 259 for receiving a mail dovetail 252 of the second jaw 138. As a result the first jaw is releasably attachable to the distal end of the first arm via engagement of a male dovetail 250 of the first jaw with an aperture 257 of the first arm and the second jaw is releasably attachable to the distal end of the link via engagement of the male dovetail 252 with the link aperture 259.

Figure 10:
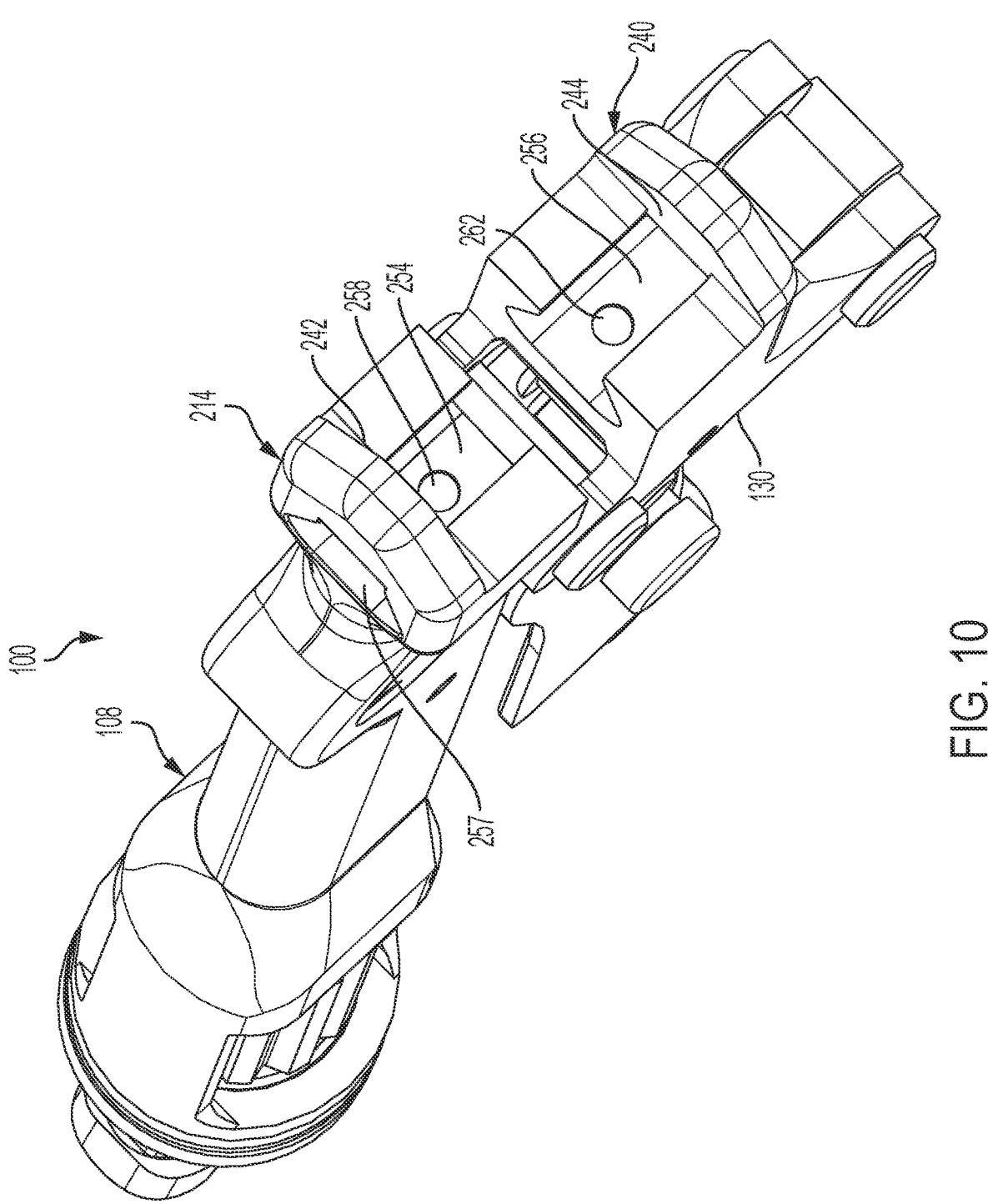
FIG. 10 is a front perspective of the surgical extractor of FIG. 1 with first and second jaws thereof omitted for purposes of clarity.

As shown in FIG. 10, the fasteners at the distal ends of the link 130 and the first arm 108 are preferably cooperating fasteners or slidable locks that respectively engage cooperating fasteners or cooperating slidable locks provided at the proximal ends of the first and second jaws, as described below.

The extractor device 100A further comprises the aforementioned biasing member 144 which is connected to and biases the link 130 and the first arm 108, in a manner described in greater detail below. The biasing member can be e.g., a tension spring, an elastomer or the like. In the present embodiment, the tension spring has a spring constant of about 0.5 to 8.0 lbs, including 0.4, 0.6, 0.7, 0.8, 0.9, 1.0, 2.0, 3.0, 4.0, 5.0, 6.0, 7.0, and 9.0 lbs.

Figure 11:
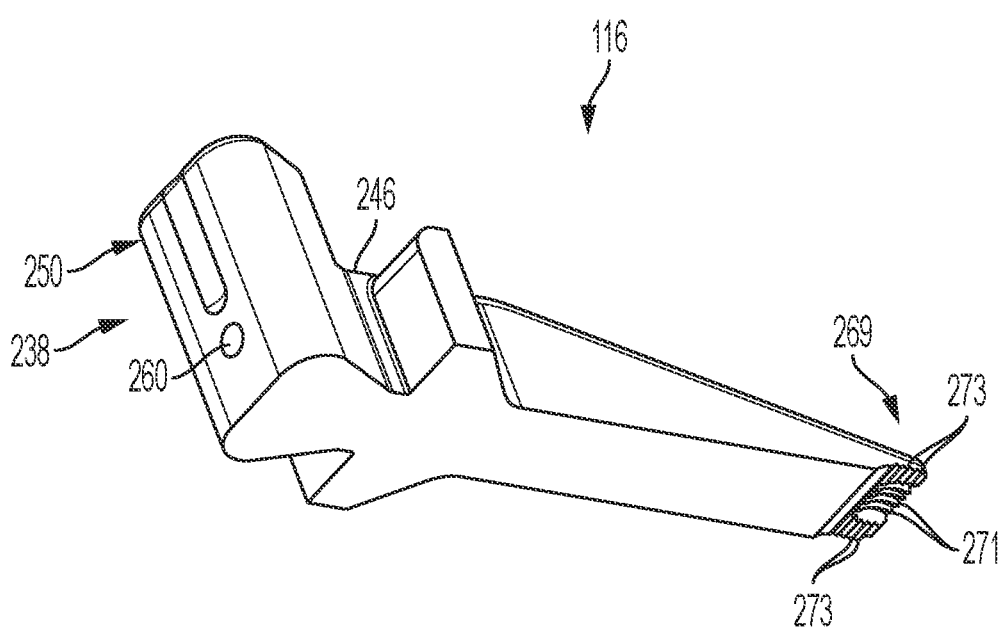
FIG. 11 is a perspective view of a first jaw of the surgical extractor of FIG. 1.
Figure 12:
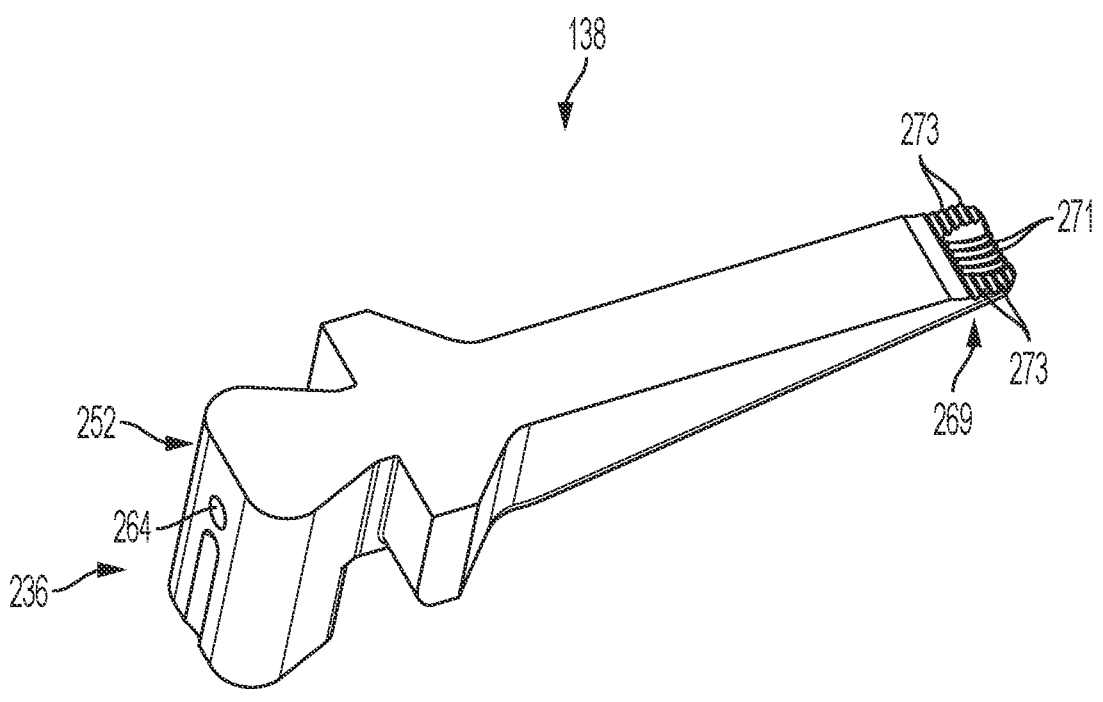
FIG. 12 is a perspective view of a second jaw of the surgical extractor of FIG. 1.

The first and second jaws respectively are structured as best shown in FIGS. 11 and 12. The first and second jaws respectively include a corresponding recess 260 and 264 to releasably engage respective corresponding detents 258, 262 (FIG. 10) on the distal ends of the first arm and the link. The first and second jaws respectively include slidable locks 236 and 238 to slidingly engage a corresponding slidable lock 214, 240 on the first arm 108 and link 130, respectively, as shown in FIG. 10. Still referring to FIG. 10, the corresponding slidable locks on the first arm and link each includes a stop 242, 244. According to an aspect, the stops 242, 244 are distally extending ledges. The stops 242, 244 are engageable by flats 246, 248 respectively provided on the first and second jaws (FIGS. 11 and 12) to limit insertion of the first and second jaws into the first arm and the link.

According to another aspect, the slidable lock 236 and 238 on each of the first and second jaws is the male dovetail 250 and 252, respectively (FIGS. 11 and 12), and the corresponding slidable lock 214, 240 on each of the first arm and the link is a female dovetail 254 and 256, respectively (FIG. 10). The first and second jaws are thus inserted from inner or medial sides of the first arm and the link towards their outer or lateral sides thereof, whereby the flats 246, 248 stop the slidable locks from further insertion upon engagement with the stops 242, 244. Additionally, the male dovetails 250, 252 of the jaws have longitudinal lengths whereby, when inserted into the female dovetails 254, 256, the male dovetails project outwardly of the first arm and the link, as shown in FIG. 1.

According to another aspect, the extractor device further comprises a detent 258 (FIG. 10) carried by one of the first jaw and the first arm, or a detent 262 carried by the one of the second jaw and the link. In the illustrated exemplary embodiment, the detent 258 is carried by the first arm for engaging a corresponding recess 260 in the first jaw, and the detent 262 is carried by the link for engaging corresponding recess 264 in the second jaw (FIGS. 10 and 12). An exemplary detent can be e.g., a ball detent. As shown in FIG. 3, the detents 258, 262 are urged outwardly toward engagement with recesses 260, 264 by biasing members 266 and 268, such as springs or the like. Engagement of the detents with their corresponding recesses operates to resist inadvertent dislodgement of the first and second jaws from the first arm and the link. When it is desired to release the jaws from the first arm and the link, the user presses against the outwardly projecting male dovetails 250, 252 with sufficient force to overcome the biasing force of the biasing members 266, 268, whereby the detents become dislodged from the recesses.

As shown in FIGS. 11 and 12, a nose or bite portion 269 of each of the first and second jaws 116, 138 is provided with a plurality of longitudinally extending ridges 271 and a plurality of ridges 273 extending transversely to the plurality of longitudinally extending ridges. The ridges 271, 273 serve to firmly bite into the fastener 142 (FIG. 1) when the jaws 116, 138 are clamped thereon. As noted above, fastener 142 may be a bone screw or the like, or any sort of fastener such as a nut which requires a rotational motion to extract it from bone or and implant. As such, depending on the type of fastener to be extracted, the nose or bite portion 269 of the first and second jaws may be provided with differently constructed ridges or other formations suitable to bite into and extract the fastener.

Figure 13:
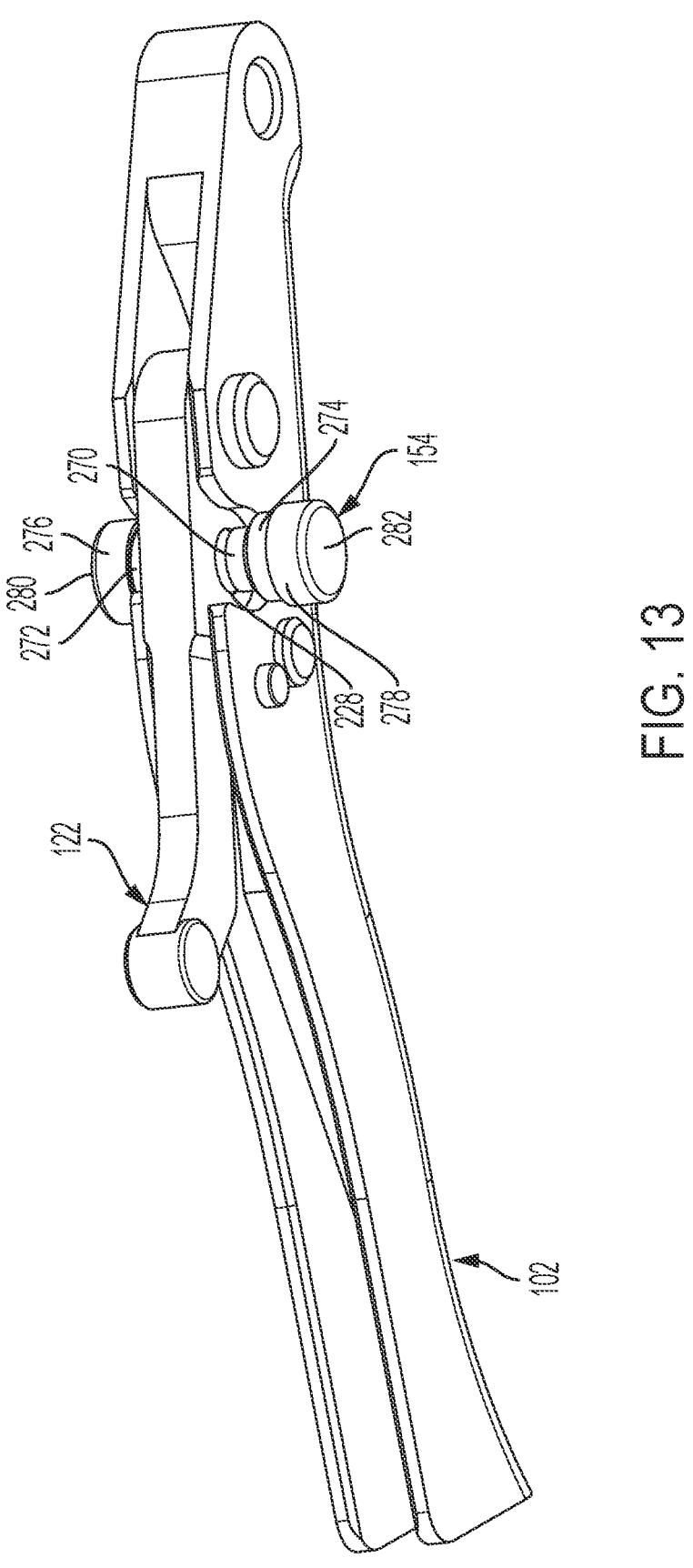
FIG. 13 is a perspective view of the lever, the second arm and the locking mechanism of the surgical extractor of FIG. 1 in an unlocked position.
Figure 14:
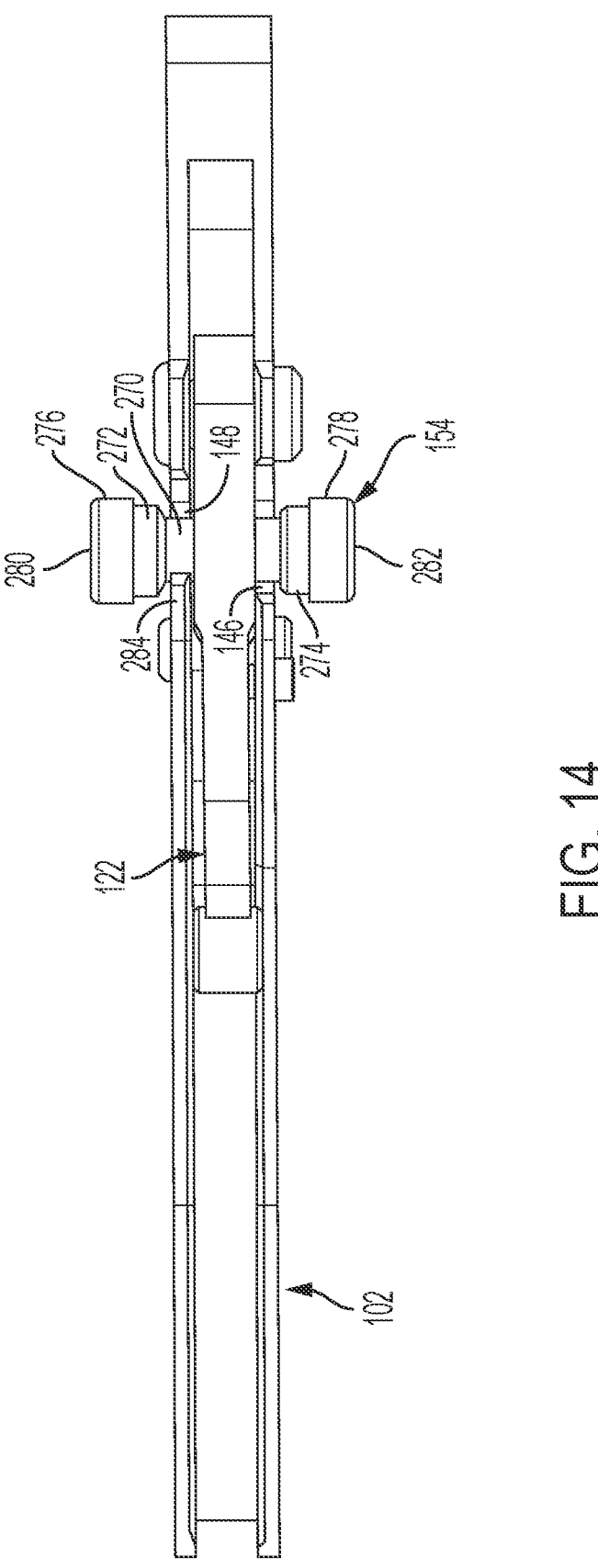
FIG. 14 is a top view of the lever, the second arm and the locking mechanism of FIG. 13 in an unlocked position.
Figure 15:
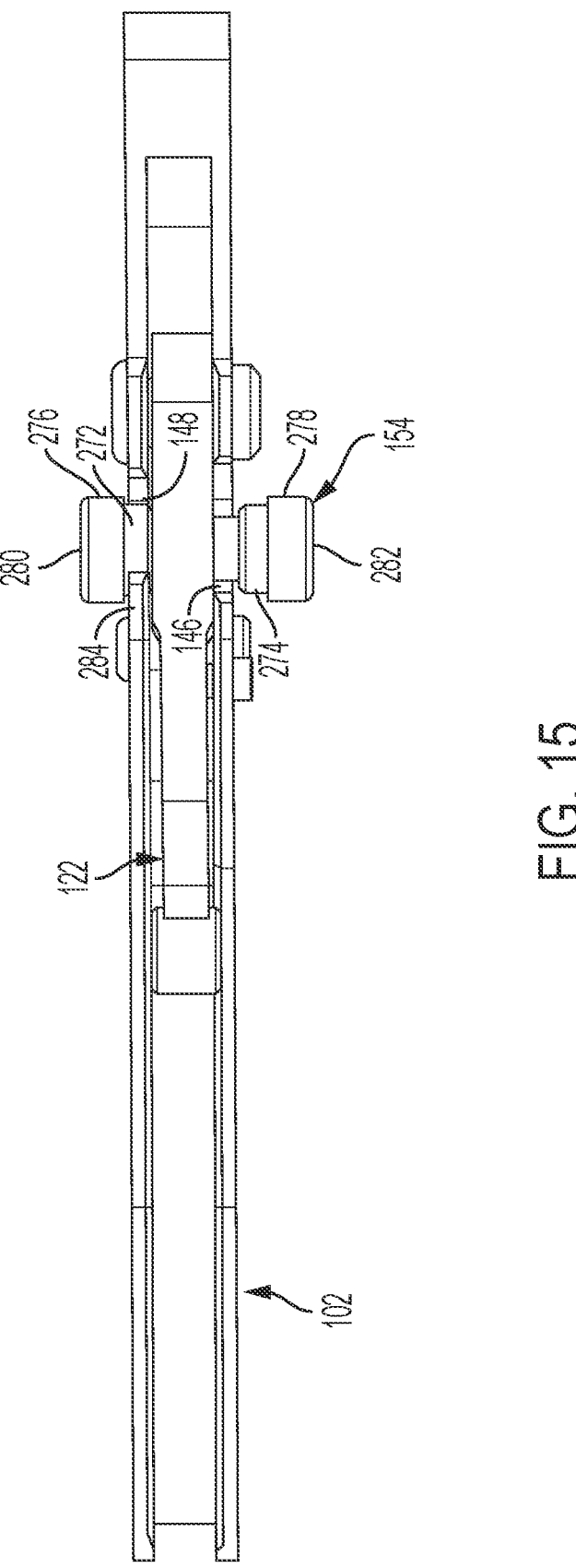
FIG. 15 is a top view of the lever, the second arm and the locking mechanism of FIG. 13 in a locked position.

The locking mechanism 154 is configured as best shown in FIGS. 13-15. The locking mechanism 154 is carried by the lever 122. That is, the locking mechanism is on the lever and movable between a locked position and an unlocked position. In the locked position (FIG. 15), the locking mechanism maintains clamping engagement of the first and second jaws and, in the unlocked position (FIGS. 13 and 14), the locking mechanism permits release of the first and second jaws from clamping engagement with a fastener to be extracted.

The locking mechanism includes a central shaft 270 sized to reciprocate within the through bore 228 of the lever 122. At opposite ends of the central shaft 270, the locking mechanism includes first cylindrical portions 272, 274 of larger diameter than the central shaft that are sized to be received in notches 146, 148 provided in the upstanding side walls of the second arm 102. Additionally, adjacent the outside or lateral ends of the first cylindrical portions are second cylindrical portions or buttons 276, 278 of larger diameter than the first cylindrical portions. The outer surfaces 280, 282 of the buttons 276, 278 are adapted to be pressed by a user's finger.

To place the locking mechanism 154 into the locked position, the user presses the outer surface 280 of the button 276 until the first cylindrical portion 272 is received in notch 148 (FIG. 15). The notch 148 includes an overhang 284 which overlies the first cylindrical portion 272. The overhang prevents dislodgement of the cylindrical portion 272 from the notch 148 and secures the second arm 102 and the lever 122 connected thereto into a locked position.

To place the locking mechanism 154 into the unlocked position, i.e., to release the locking mechanism from the locked position, a user presses the outer surface 282 of the button 278 until the first cylindrical portion 272 is no longer received in the notch 148 and retained by the overhang 284. With the locking mechanism 154 in such position, the user can separate the second arm from the first arm whereby the first and second jaws are released from clamping engagement with the fastener 142.

Figure 16:
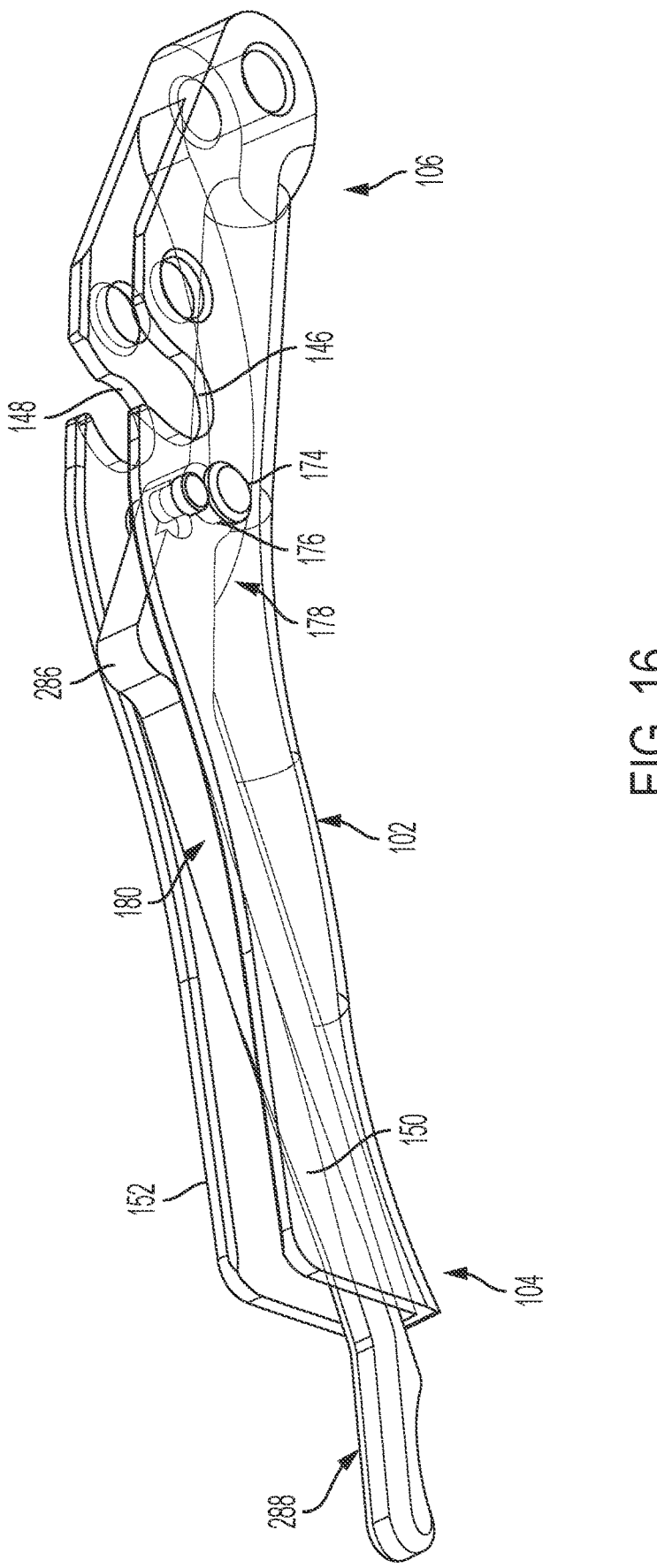
FIG. 16 is a perspective view of a release lever and the second arm of the surgical extractor of FIG. 1.

The extractor device 100A further comprises a release lever 180 (FIG. 16) on the second arm 102 to release the first and second jaws from clamping engagement with an implant to be extracted. The release lever has a knuckle 286 provided adjacent the distal end 178 thereof, and a proximal end 288 projecting from the proximal end 104 of the second arm. Before deploying the release lever, the user must place the locking mechanism 154 oriented in the unlocked position. The proximal end 288 of the release lever is lifted upwardly (as shown in FIG. 16) until the knuckle 286 contacts the underside of the lever 122. Further lifting of the release lever operates to withdraw the locking mechanism from the notches 146, 148 and push the second arm 102 away from the first arm 108, thereby allowing the first and second jaws to spread apart.

In order to clamp the first and second jaws onto a fastener to be extracted, a user first rotates the rotatable knob 196 in a first direction which causes the first and second jaws to separate until opposed bite portions 269 at respective distal ends of the first and second jaws (FIGS. 11 and 12) are spaced slightly wider than the circumference of the fastener to be extracted. More particularly, rotation of the rotatable knob in the first direction causes the distal end 126 of the lever and the second arm 102 to move rearwardly, whereby the link 130 pivots rearwardly and the second jaw 138 moves away from the first jaw 116. The user then places the opposed bite portions 269 adjacent the fastener and rotates the rotatable knob in the opposite direction which causes the first and second jaws to close around the fastener. More particularly, rotation of the rotatable knob in the opposite direction causes the distal end 126 of the lever and the second arm 102 to move forwardly, whereby the link 130 pivots forwardly causing the second jaw 138 to move toward the first jaw 116. Additionally, the biasing member 144 keeps the first and second jaws open during clamping of the fastener 142. That is, the biasing member serves to prevent the second jaw from uncontrolled movement which could hinder clamping of the first and second jaws to the fastener. The user then squeezes the first and second arms together whereupon the second arm pivots posteriorly until the locking mechanism 154 becomes seated in the notches 146, 148 of the second arm. During seating of the locking mechanism into the notches, the first and second jaws are urged into tight clamping engagement with the fastener 142. Once the locking mechanism is fully seated in the notches, the user presses the outer surface 280 of the button 276 until the first cylindrical portion 272 is received in the notch 148, thereby locking the position of the second arm relative to the first arm. With the second arm locked and the implant extractor 100 secured to the implant, the user may use the ratchet handle device 100B, described below, to unscrew the fastener from the bone to which it is attached. Once the fastener is freed, the user unlocks the locking mechanism 154 and lifts the proximal end 284 of the release lever to open the first and second jaws and release the fastener from the extractor device 100A.

Figure 17A:
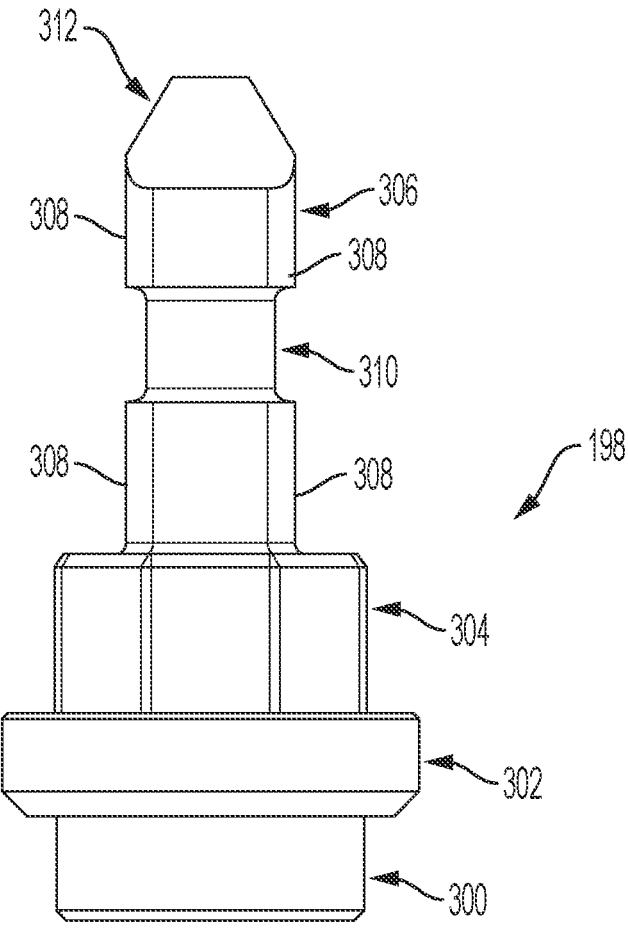
FIG. 17A is a side view of a quick connect of the surgical extractor of FIG. 1.
Figure 17B:
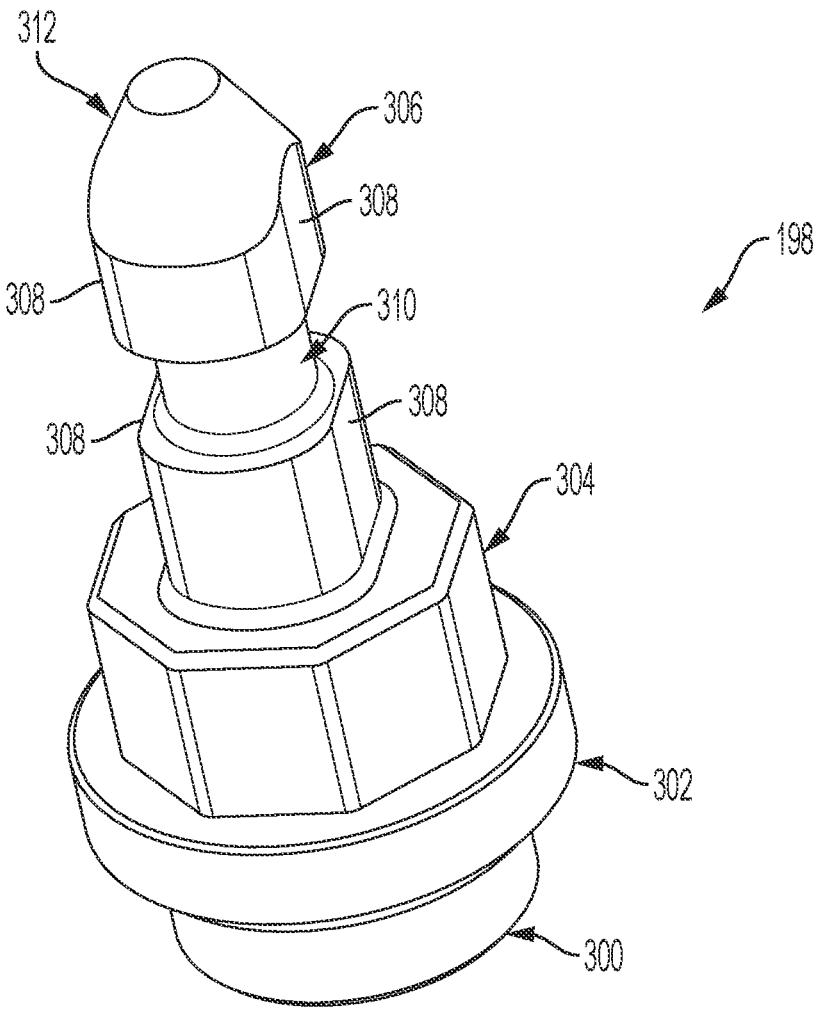
FIG. 17B is a rear perspective view of the quick connect of FIG. 17A.
Figure 17C:
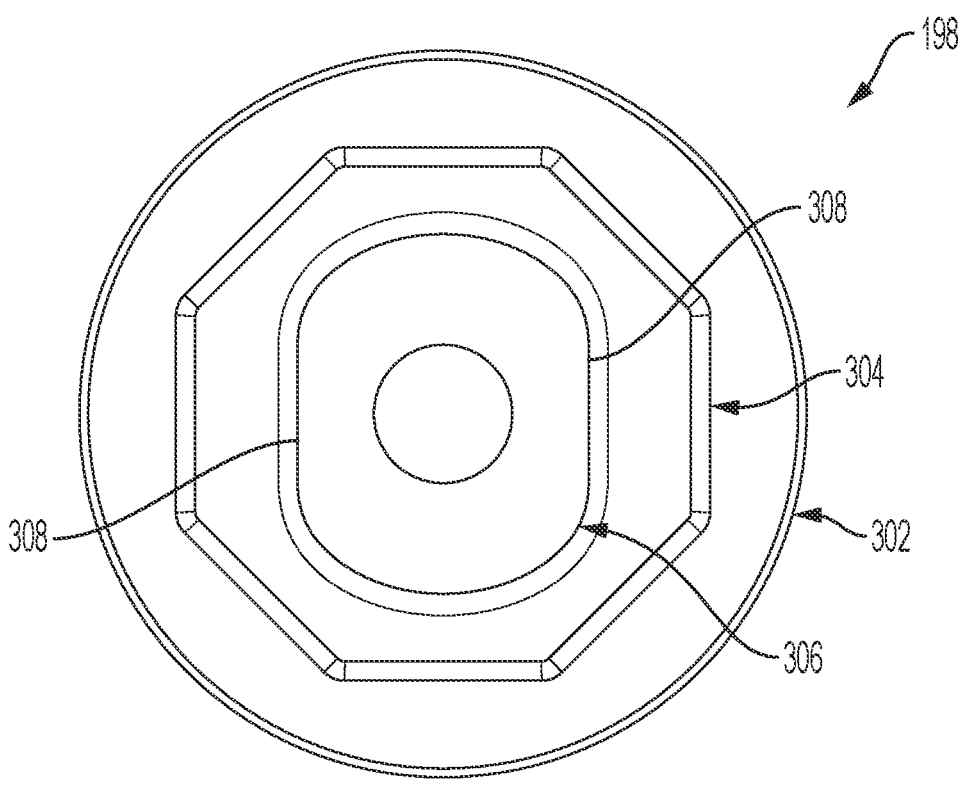
FIG. 17C is a rear end view of the quick connect of FIG. 17A.

Referring to FIGS. 17A-17C, there is shown an exemplary embodiment of the quick connect 198 which may be releasably or fixedly connected to the proximal end of the first arm 108 of the extractor device 100A. In this regard, the quick connect comprises a distal portion 300 that is configured for insertion into the proximal end of the first arm of the extractor device. Adjacent the distal portion 300 is an enlarged annular portion 302 which functions as a stop for limiting insertion of the distal portion into the first arm of the extraction device. Once inserted in the first arm, the quick connect 198 may be affixed thereto by any suitable affixation technique including, without limitation, welding or adhesives. On the proximal side of the enlarged annular portion 302 is a polygonal portion 304. Proximal to the polygonal portion is a shaft 306 having an oval peripheral shape with oppositely directed flat surfaces 308. Shaft 306 includes a reduced diameter central portion 310 having a circular peripheral shape. A proximal end 312 of the shaft 306 is preferably tapered to facilitate insertion of the shaft into a correspondingly shaped oval aperture 314 provided in a housing 316 (FIGS. 18B, 18C and 19) of a ratchet assembly 350 (FIG. 24) of the ratchet handle device 100B. The tapered proximal end 312 of the shaft 306 also operates to displace the biased locking member 199 until it comes into engagement with the reduced diameter central portion 310 (FIG. 20), thereby locking the shaft 306 to the housing 316 and preventing relative rotation therebetween, the purpose of which is described in greater detail below.

Figure 22:
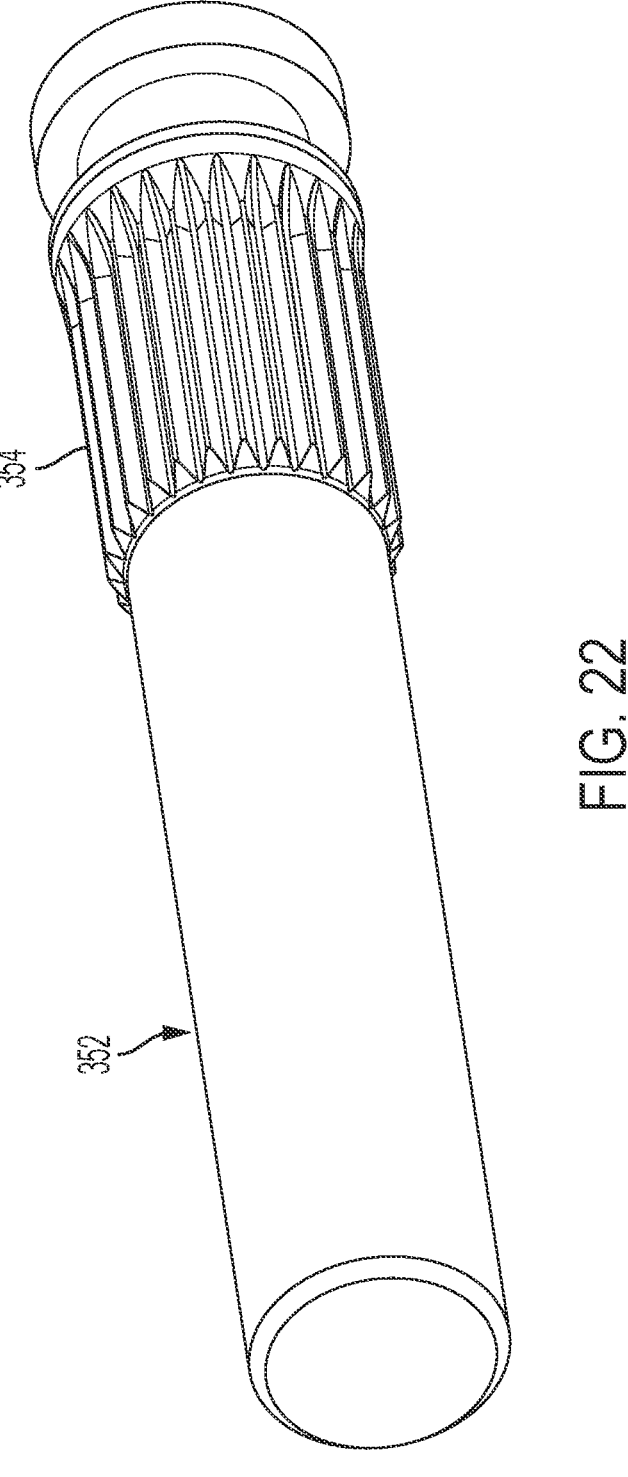
FIG. 22 is a perspective view of a ratchet handle shaft of the surgical extractor of FIG. 1.

The ratchet handle device 100B comprises the ratchet assembly 350, a handle shaft 352 including splines 354, wherein the handle shaft 352 extends proximally from the ratchet assembly (FIGS. 22-24), and a quick connect coupling 199' (FIG. 20). In an exemplary embodiment, the quick connect coupling can be a female coupling including the biased locking member 199 for engaging the quick connect 198 of the first arm 108, in particular the reduced diameter central portion 310 of shaft 306.

Figure 18A:
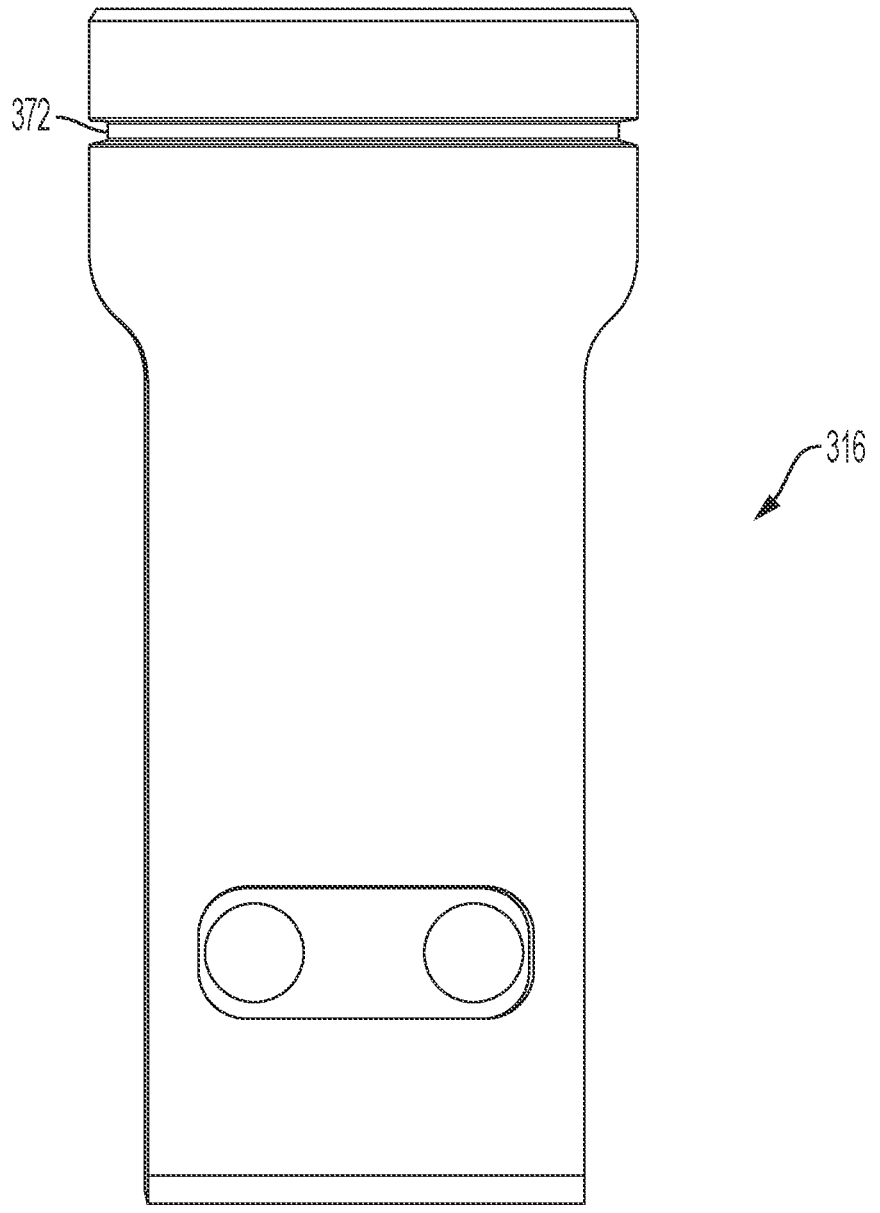
FIG. 18A is a side view of a ratchet housing of the surgical extractor of FIG. 1.
Figure 18B:
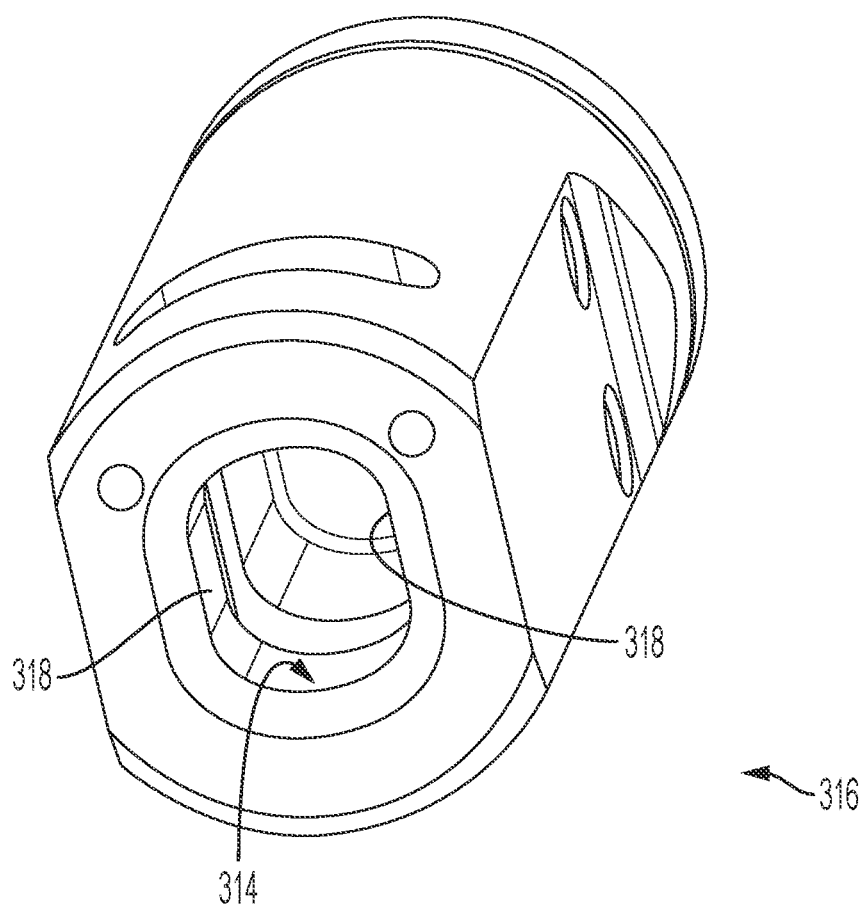
FIG. 18B is front perspective the ratchet housing of FIG. 18A.
Figure 18C:
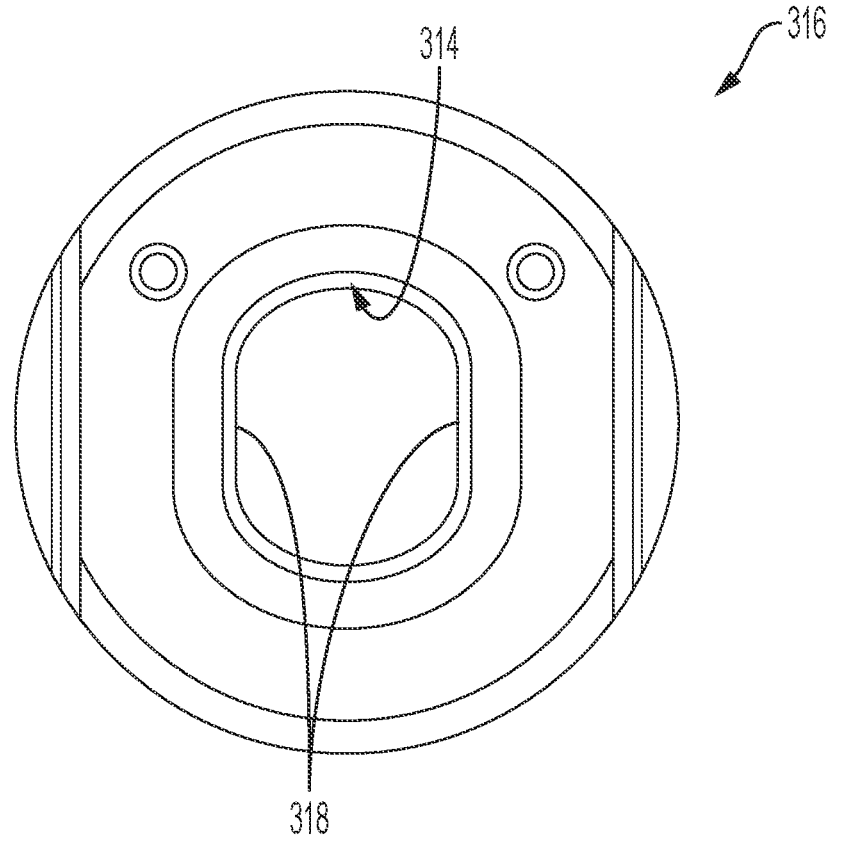
FIG. 18C is a front end view of the ratchet housing of FIG. 18A.
Figure 19:
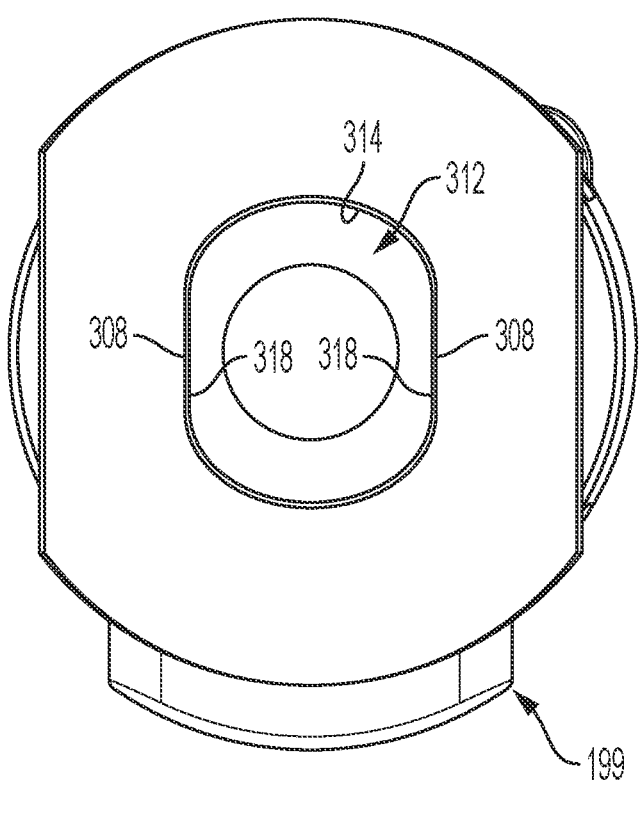
FIG. 19 is a cross-sectional view taken along line 19-19 of FIG. 2 showing the mating relationship of the quick connect of FIGS. 17A-17C with the ratchet housing of FIGS. 18A-18C.

FIGS. 1-3, 18A-18C and 19 illustrate an exemplary construction of the housing 316. Referring in particular to FIGS. 18B and 18C, there is shown the oval aperture 314 which includes opposed flat surfaces 318. That is, housing comprises opposed flat surfaces 318 and the quick connect 198 of the first arm comprises oppositely directed flat surfaces 308 configured to matingly engage with the opposed flat surfaces of the housing to prevent relative rotation between the housing and the extractor device. As a result, when the ratchet handle device 100B is coupled with extractor device 100A by virtue of the biased locking member 199 engaging the reduced diameter central portion 310 of the shaft 306, the mating engagement of the shaft 306 with the oval aperture 314 permits a user to rotate the ratchet handle device 100B and the extractor device 100A in unison in a direction or directions dictated by the ratchet assembly 350, described below.

Figure 23:
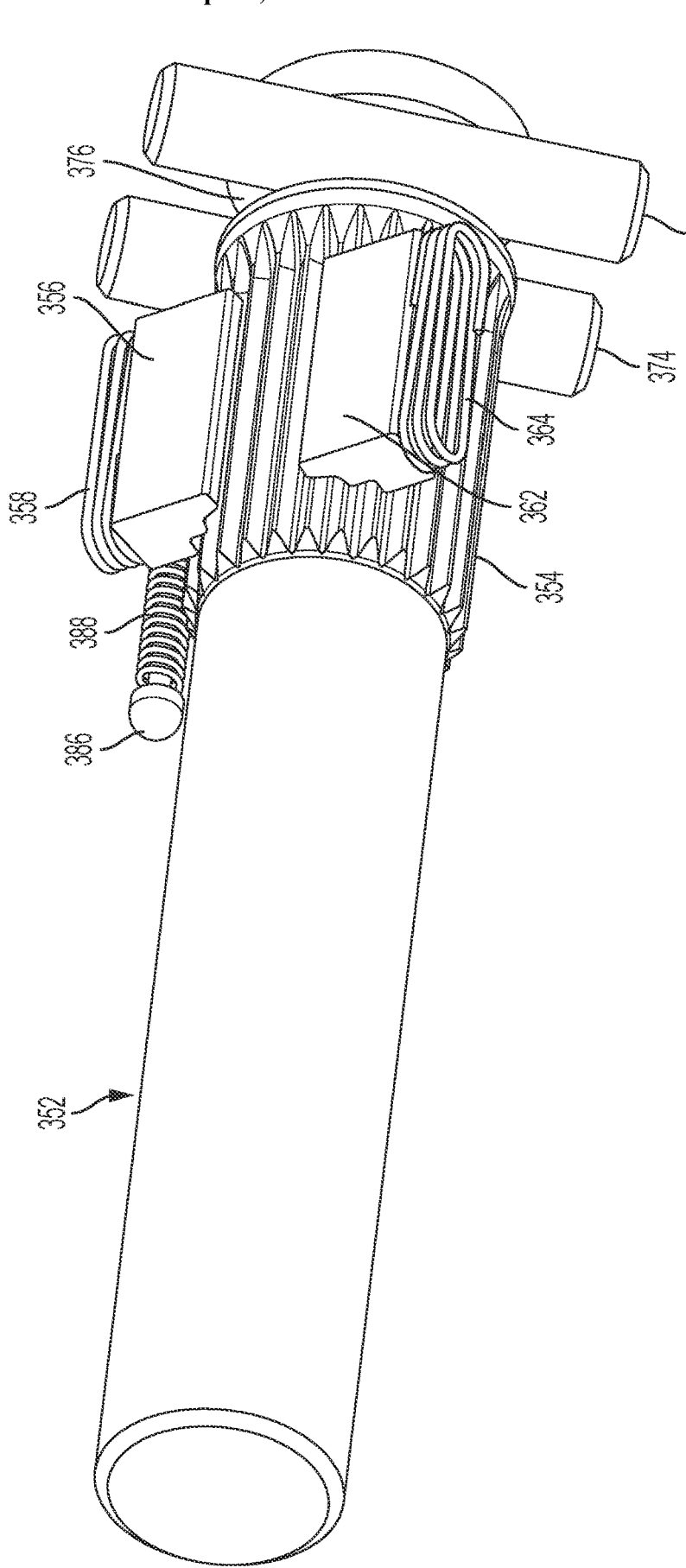
FIG. 23 is a perspective view of the ratchet handle shaft of FIG. 22 including ratchet pawls, ratchet pawl biasing members, a biased ball detent and ratchet handle shaft anchoring pins.
Figure 24:
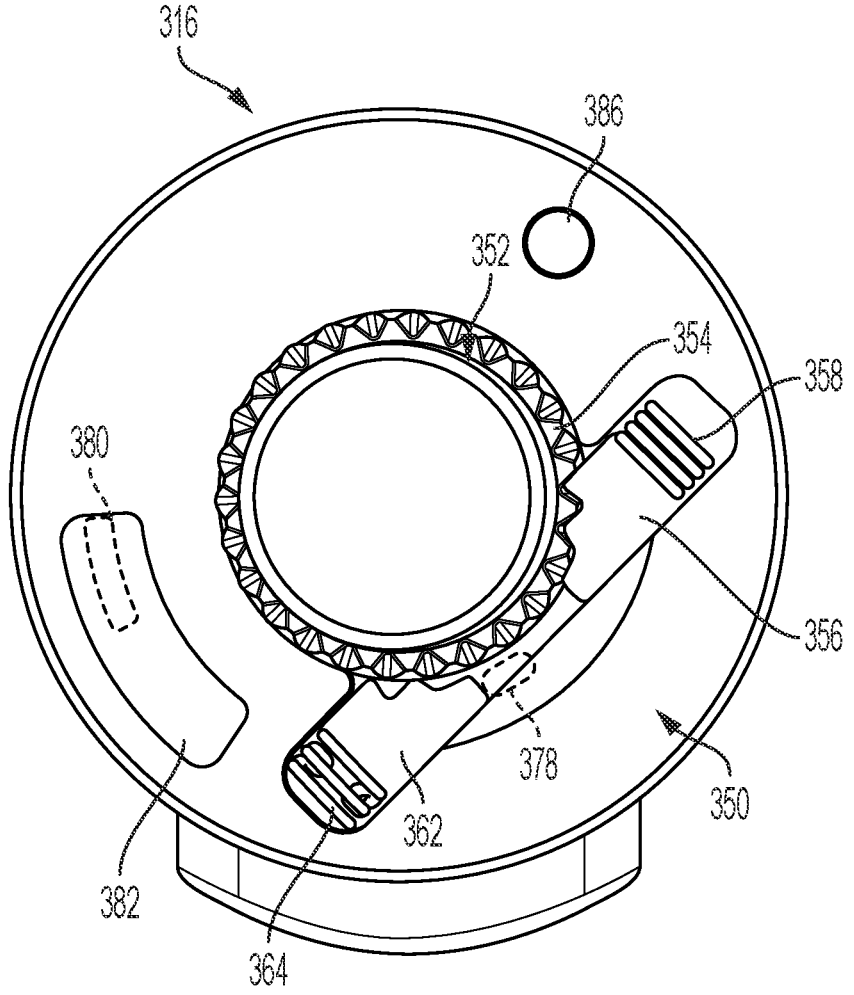
FIG. 24 is a rear end view of an assembled ratchet handle device with the ratchet direction selection cap and a grip member of the ratchet handle shaft omitted for purposes of clarity.

According to an exemplary embodiment of the subject disclosure, as illustrated in FIGS. 23 and 24, the ratchet assembly 350 comprises the housing 316, and a first pawl 356 within the housing configured to engage the handle shaft splines 354 from a first direction and arrest rotation of the handle shaft 352 in a first rotational direction. The ratchet assembly further includes a first biasing member 358, e.g., a spring, an elastomer or the like, within the housing biasing the first pawl 356 into engagement with the handle shaft splines 354. Constructed as such, the ratchet assembly 350 permits a clamped fastener to be unscrewed in a first rotational direction when the ratchet handle device 100B is connected to the extractor device 100A. In this regard, to facilitate turning of the handle shaft 352, the handle shaft includes a grip 360 at a proximal end thereof which extends substantially transverse to the handle shaft.

According to a further exemplary embodiment, the ratchet assembly 350 further comprises a second pawl 362 within the housing 316 configured to engage the handle shaft splines 354 from a second direction opposite the first direction that the first pawl 356 engages the handle shaft splines. When the second pawl is engaged with the handle shaft splines it arrests rotation of the handle shaft 352 in a second rotational direction opposite the first rotational direction thereof. The ratchet assembly further includes a second biasing member 364, e.g., a spring, an elastomer or the like, within the housing biasing the second pawl 362 into engagement with the handle shaft splines 354. Constructed as such, the ratchet assembly 350 permits a clamped fastener to be unscrewed in either a first rotational direction or a second rotational direction, depending on the direction of the fastener threading, when the ratchet handle device 100B is connected to the extractor device 100A.

Figure 21:
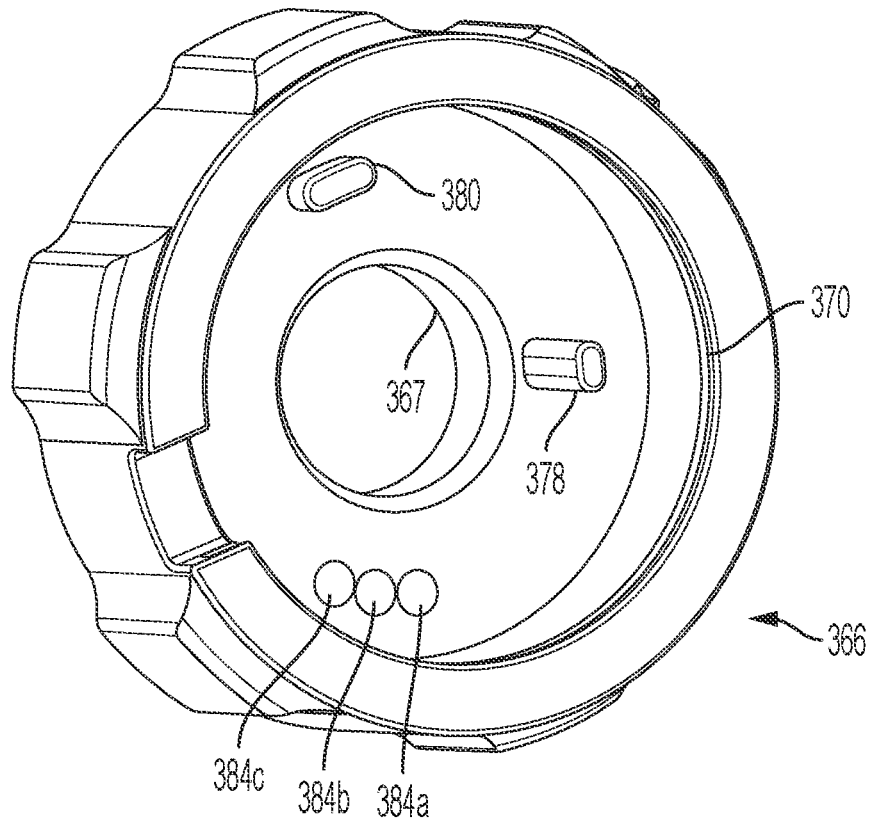
FIG. 21 is a perspective view of the underside of a ratchet direction selection cap of the surgical extractor of FIG. 1.

FIG. 21 illustrates the undersurface of a control cap 366 (also shown in FIGS. 1-3) which is part of the ratchet assembly 350. The control cap includes a central opening 367 through which the handle shaft 252 extends. The control cap serves to permit selective rotation of the handle shaft relative to the ratchet assembly in either the first rotational direction or the second rotational direction. The control cap 366 is rotatably retained on the housing 316 by a retainer ring 368 (FIG. 3) which resides in an annular groove 370 provided in the control cap (FIG. 21) and a corresponding annular groove 372 provided in the housing 316 (FIG. 18A). In addition, a pair of retainer pins 374 are positioned in an annular groove 376 provided adjacent a distal end of the handle shaft 352 (FIG. 23) and are configured to engage unillustrated recesses in an inner wall of the housing 316. The retainer pins 374 serve to anchor the handle shaft 352 to the housing 316 (while permitting rotation of the handle shaft by virtue of the annular groove 376) in order to resist separation of the handle shaft from the housing when a user pulls the grip 360 in a proximal direction during fastener extraction.

Referring again to FIG. 21, the undersurface of the control cap 366 includes several formations, each of which performs a separate function in the ratchet assembly 350. A first formation is a first projection or actuator 378 which stands proud of the undersurface of the control cap. The distance the actuator 378 projects from the undersurface of the control cap is sufficient for the actuator to extend between the first and second pawls 356, 362, as indicated by dashed line 378 in FIG. 24. As described in greater detail below, the actuator 378 is operable to selectively disengage the first pawl and the second pawl 356, 362 from the handle shaft splines 354 to permit rotation of the handle shaft 352 in either the first rotational direction or the second rotational direction. That is, the control cap enables selective reversible ratcheting rotation of the handle shaft. A second formation is an angular motion limiter 380 which also stands proud of the undersurface of the control cap. The distance the angular motion limiter 380 projects from the undersurface of the control cap is sufficient for the angular motion limiter to reside in an arc-shaped recess 382 provided in the housing 316, as indicated by dashed line 380 in FIG. 24. A third formation is a plurality, e.g., three, recesses 384*a*, 384*b* and 384*c* in the undersurface of the control cap, each of which are configured to receive a ball detent 386 (FIGS. 23 and 24) which is biased into selective seating engagement with one of the 384*a*, 384*b* and 384*c* by a biasing member 388, e.g., a spring or an elastomer (FIG. 23).

Prior to operation, with the control cap 366 rotatably secured to the housing 316 and the ratchet handle device 100B connected to the extractor device 100A, the ball detent 386 typically rests in the center or "neutral" recess 384*b* whereby the actuator 378 does not contact either the first pawl 356 or the second pawl 362 and both pawls are in engagement with the handle shaft splines 354 such that the handle shaft is prevented from rotating. The user then rotates the control cap 366 in a clockwise or counterclockwise direction such that the ball detent 386 comes to rest in one of the recesses 384*a* or 384*c*. As a result of this action, the actuator 378 moves into contact with either the first pawl 356 or the second pawl 362 to disengage the contacted pawl from the handle shaft splines 354, whereby the non-contacted pawl remains in engagement with the handle shaft splines, such that the handle shaft, and thus the fastener 142 clamped by the extraction device 100A, may be rotated in ratcheting fashion in either a first or a second rotational direction. This situation is depicted in FIG. 24 which shows the actuator 378 (in dashed line) in contact with the second pawl 362 whereby the second pawl disengages from the handle shaft splines 354. When reverse ratcheting rotation of the handle shaft 352 (and the fastener 142 clamped by the extraction device 100A) is desired, the user simply rotates the control cap in the opposite direction until the ball detent 386 comes to rest in the other of recesses 384*a* or 384*c* and the actuator 378 moves the other of the first and second pawls 356, 362 from engagement with the handle shaft splines 354.

It will be appreciated by those skilled in the art that changes could be made to the embodiments described above without departing from the broad inventive concept thereof. It is to be understood, therefore, that this invention is not limited to the particular embodiments disclosed, but it is intended to cover modifications within the spirit and scope of the present invention as defined by the appended claims.

We claim:

1. A surgical extractor comprising:
an extractor device having a proximal end and a distal end;
a first jaw and a second jaw configured to engage a fastener and carried at the distal end of the extractor device; and
a ratchet handle device extending from the proximal end of the extractor device,
wherein the extractor device comprises:
a first arm having a proximal end and a distal end, a quick connect at the proximal end thereof for operatively engaging the ratchet handle device, the distal end of the first arm being configured for attachment to the first jaw,
a second arm, and
a link pivotably connected to the first and second arms, wherein the link has a distal end configured for attachment to the second jaw,
and wherein the ratchet handle device comprises:
a ratchet assembly,
a handle shaft including splines, wherein the handle shaft extends proximally from the ratchet assembly, and
a quick connect coupling for engaging the quick connect of the first arm,
the ratchet assembly comprising:
a housing,
a first pawl within the housing configured to engage the handle shaft splines from a first direction and arrest rotation of the handle shaft in a first rotational direction,
a first biasing member within the housing biasing the first pawl into engagement with the handle shaft splines,
a second pawl within the housing configured to engage the handle shaft splines from a second direction opposite the first direction and arrest rotation of the handle shaft in a second rotational direction opposite the first rotational direction,
a second biasing member within the housing biasing the second pawl into engagement with the handle shaft splines, and
an actuator extending between the first pawl and the second pawl for selectively disengaging the first pawl and the second pawl from the handle shaft splines to permit rotation of the handle shaft in either the first rotational direction or the second rotational direction.

2. The surgical extractor of claim 1, wherein the handle shaft is operable to rotate relative to the ratchet assembly.

3. The surgical extractor of claim 1, wherein the housing comprises opposed flat surfaces and the quick connect of the first arm comprises oppositely directed flat surfaces configured to matingly engage with the opposed flat surfaces of the housing to prevent relative rotation between the housing and the extractor device.

4. The surgical extractor of claim 1, wherein the handle shaft includes a grip at a proximal end thereof.

5. The surgical extractor of claim 4, wherein the grip extends substantially transverse to the handle shaft.

6. The surgical extraction device of claim 1, wherein each of the first and second jaws comprises a plurality of longitudinally extending ridges.

7. The surgical extractor of claim 6, wherein each of the first and second jaws further comprises a plurality of ridges extending transversely to the plurality of longitudinally extending ridges.

* * * * *